US012630619B2

(12) United States Patent
Chakrabartty et al.

(10) Patent No.: US 12,630,619 B2
(45) Date of Patent: May 19, 2026

(54) IMMUNOGLOBULIN LIGHT CHAIN ANTIBODIES AND USES THEREOF

(71) Applicant: UNIVERSITY HEALTH NETWORK, Toronto (CA)

(72) Inventors: Avijit Chakrabartty, Vaughan (CA); Yulong Sun, Maple (CA); Natalie J. Galant, Kleinburg (CA); Kevin C. Hadley, Toronto (CA); Meghan A. Wing, Guelph (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 499 days.

(21) Appl. No.: 18/328,447

(22) Filed: Jun. 2, 2023

(65) Prior Publication Data
US 2024/0025977 A1 Jan. 25, 2024

Related U.S. Application Data

(63) Continuation of application No. PCT/IB2021/000897, filed on Dec. 13, 2021.

(60) Provisional application No. 63/125,281, filed on Dec. 14, 2020.

(51) Int. Cl.
*C07K 16/18* (2006.01)
*A61P 37/02* (2006.01)

(52) U.S. Cl.
CPC .............. *C07K 16/18* (2013.01); *A61P 37/02* (2018.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. |
| 4,816,567 A | 3/1989 | Cabilly et al. |
| 5,223,409 A | 6/1993 | Ladner et al. |
| 5,225,539 A | 7/1993 | Winter |
| 5,374,548 A | 12/1994 | Caras |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,476,996 A | 12/1995 | Wilson et al. |
| 5,530,101 A | 6/1996 | Queen et al. |
| 5,571,698 A | 11/1996 | Ladner et al. |
| 5,580,717 A | 12/1996 | Dower et al. |
| 5,585,089 A | 12/1996 | Queen et al. |
| 5,693,762 A | 12/1997 | Queen et al. |
| 5,698,767 A | 12/1997 | Wilson et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,180,370 B1 | 1/2001 | Queen et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 8,105,594 B2 | 1/2012 | Solomon et al. |
| 2010/0069614 A1 | 3/2010 | Houtzager et al. |
| 2012/0070861 A1 | 3/2012 | Macdonald et al. |
| 2012/0073004 A1 | 3/2012 | Macdonald et al. |

FOREIGN PATENT DOCUMENTS

| | | |
|---|---|---|
| WO | WO-0243478 A2 | 6/2002 |
| WO | WO-2009015777 A1 | 2/2009 |
| WO | WO-2011072204 A1 | 6/2011 |
| WO | WO-2011097603 A1 | 8/2011 |
| WO | WO-2011163311 A1 | 12/2011 |
| WO | WO-2011163314 A1 | 12/2011 |
| WO | WO-2012148873 A2 | 11/2012 |
| WO | WO-2022130023 A1 | 6/2022 |

OTHER PUBLICATIONS

Huang, Shuohao., and Masamichi Kamihira. Development of hybrid viral vectors for gene therapy. Biotechnology advances 31(2):208-223 (2013). Published Online Oct. 13, 2012.

Sun, Yulong et al. From TTR to AL: Novel Conformation-Specific Antibodies to Combat Systemic Amyloidosis PA152 (Abstract #187). Presented at International Symposium on Amyloidosis May 26-30, 2024 in Rochester, MN. https://doi.org/10.26226/m.65f9bf8ae6f73964e1d4ed41.

Sun, Yulong et al. From TTR to AL: Novel Conformation-Specific Antibodies to Combat Systemic Amyloidosis PA152 (Poster). Presented at International Symposium on Amyloidosis May 26-30, 2024 in Rochester, MN. https://doi.org/10.26226/m.65f9bf8ae6f73964e1d4ed41.

(Continued)

*Primary Examiner* — Misook Yu
*Assistant Examiner* — Alan Alfano
(74) *Attorney, Agent, or Firm* — Wilson Sonsini Goodrich & Rosati

(57) ABSTRACT

The present disclosure is directed to antibodies or antigen-binding portions thereof that specifically bind free immunoglobulin light chains (FLC), polynucleotides and vectors encoding the same, and pharmaceutical compositions comprising the same. Some aspects of the disclosure are directed to methods of measuring FLC in a biological sample comprising contacting the sample with the anti-FLC antibody. Some aspects of the disclosure are directed to methods of treating a disease or condition comprising administering the anti-FLC antibody to a subject in need thereof.

13 Claims, 24 Drawing Sheets
Specification includes a Sequence Listing.

(56) References Cited

OTHER PUBLICATIONS

Abe, M. et al. Production and Immunodiagnostic applications of antihuman light chain monoclonal antibodies. American journal of clinical pathology 100(1):67-74 (1993).

Campbell, John P. et al. Development of a highly-sensitive multiplex assay using monoclonal antibodies for the simultaneous measurement of kappa and lambda immunoglobulin free light chains in serum and urine. Journal of immunological methods 391(1-2):1-13 (2013).

Davern, Sandra. et al. Immunodiagnostic capabilities of anti-free immunoglobulin light chain monoclonal antibodies. American journal of clinical pathology 130(5):702-711 (2008).

Gertz, Morie A. et al. Results of the phase 3 VITAL study of NEOD001 (Birtamimab) plus standard of care in patients with light chain (AL) amyloidosis suggest survival benefit for mayo stage IV patients. Blood 134:3166, 1-5 (2019).

International Search Report and Written Opinion dated Jun. 3, 2022 for International Application No. PCT/IB2021/000897.

Kuriowa, Yoshimi. et al. Cloned transchromosomic calves producing human immunoglobulin. Nature Biotechnology 20(9):889-894 (2002).

Li, Feng. et al. Cell Culture Processes for Monoclonal Antibody Production. MAbs. 2(5):466-477 (2010).

Milani, Paolo. et al. Serum-free light-chain analysis in diagnosis and management of multiple myeloma and related conditions. Scandinavian Journal of Clinical and Laboratory Investigation 76(sup245):S113-S118 (2016).

PCT/IB2021/000897 International Preliminary Report on Patentability dated Jun. 29, 2023.

Popkova, Tereza. et al. Monoclonal antibodies in the treatment of AL amyloidosis: co-targetting the plasma cell clone and amyloid deposits. British Society for Haematology 189(2):228-238 (2020).

Renz, Mark. et al. 2A4 binds soluble and insoluble light chain aggregates from AL amyloidosis patients and promotes clearance of amyloid deposits by phagocytosis. Amyloid 23(3):168-177 (2016).

Tomizuka, K. et al. Double trans-chromosomic mice: Maintenance of two individual human chromosome fragments containing Ig heavy and κ loci and expression of fully human antibodies. Proc. Natl. Acad. Sci. USA 97(2):722-727 (2000).

UniProtKB Accession No. P0DOX7. Immunoglobulin kappa light chain. Record created Mar. 15, 2017. pp. 1-7. Retrieved Feb. 6, 2025 at URL: https://www.uniprot.org/uniprotkb/P0DOX7/entry.

UniProtKB Accession No. P0DOX8. Immunoglobulin lambda-1 light chain. Record created Mar. 15, 2017. pp. 1-7. Retrieved Feb. 6, 2025 at URL: https://www.uniprot.org/uniprotkb/P0DOX8/entry.

FIG. 1B

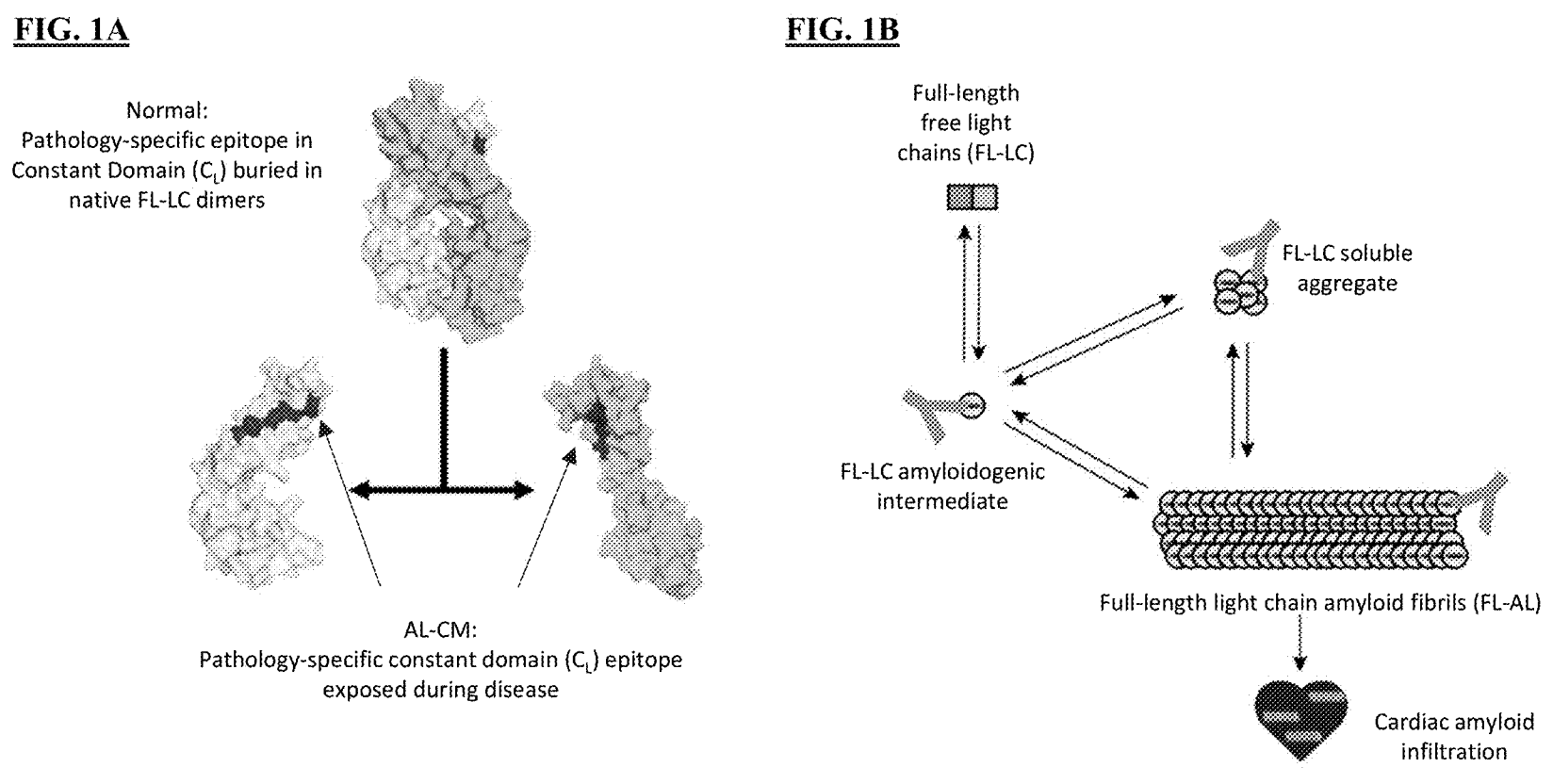

Full-length
free light
chains (FL-LC)

FL-LC amyloidogenic
intermediate

FL-LC soluble
aggregate

Full-length light chain amyloid fibrils (FL-AL)

Cardiac amyloid
infiltration

FIG. 1A

Normal:
Pathology-specific epitope in
Constant Domain (C_L) buried in
native FL-LC dimers AL-CM:
Pathology-specific constant domain (C_L) epitope
exposed during disease

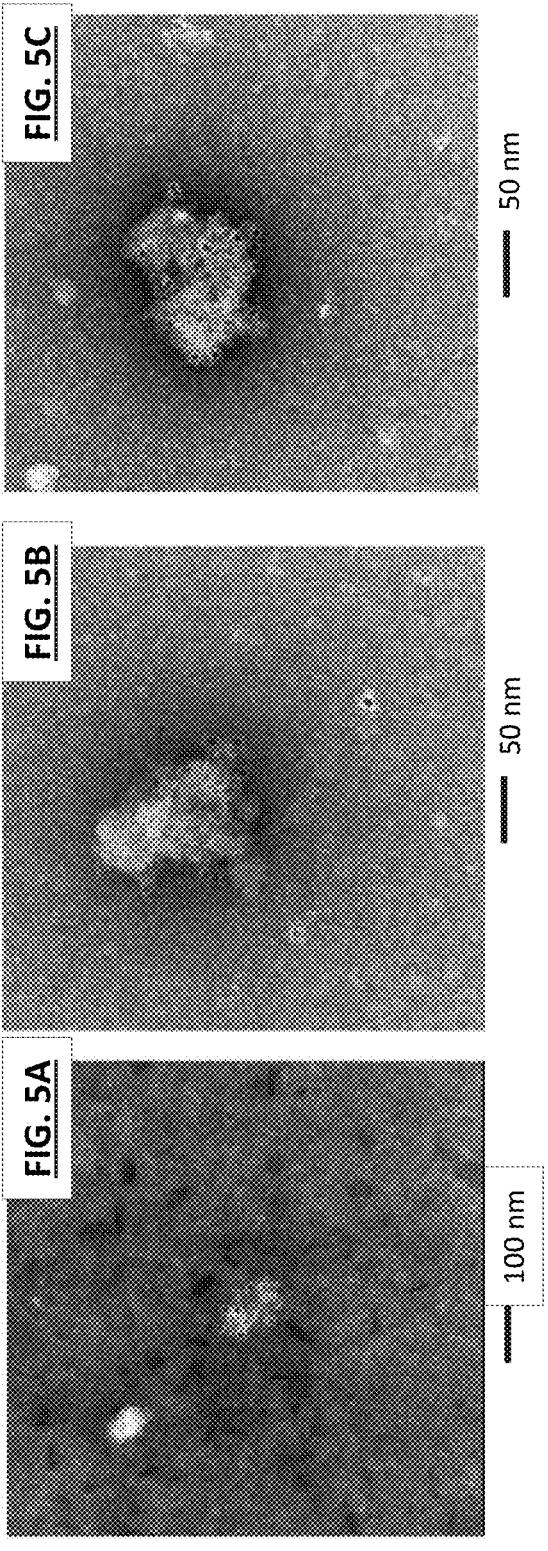

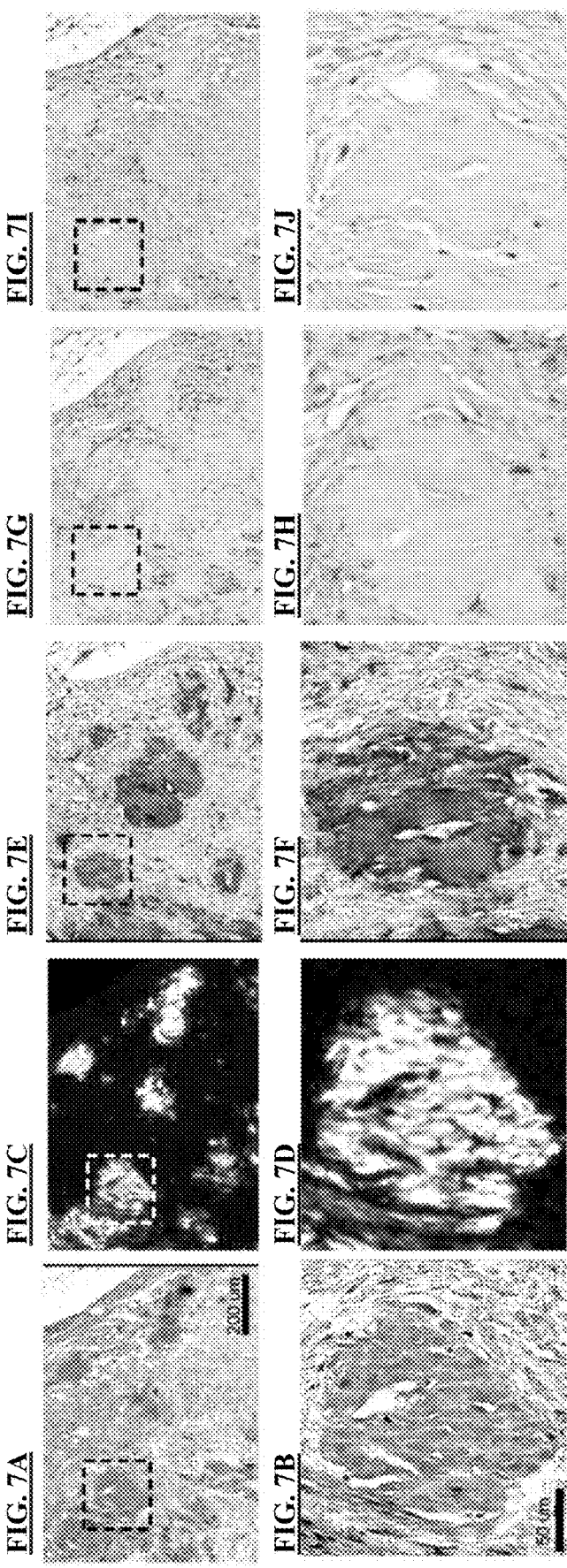

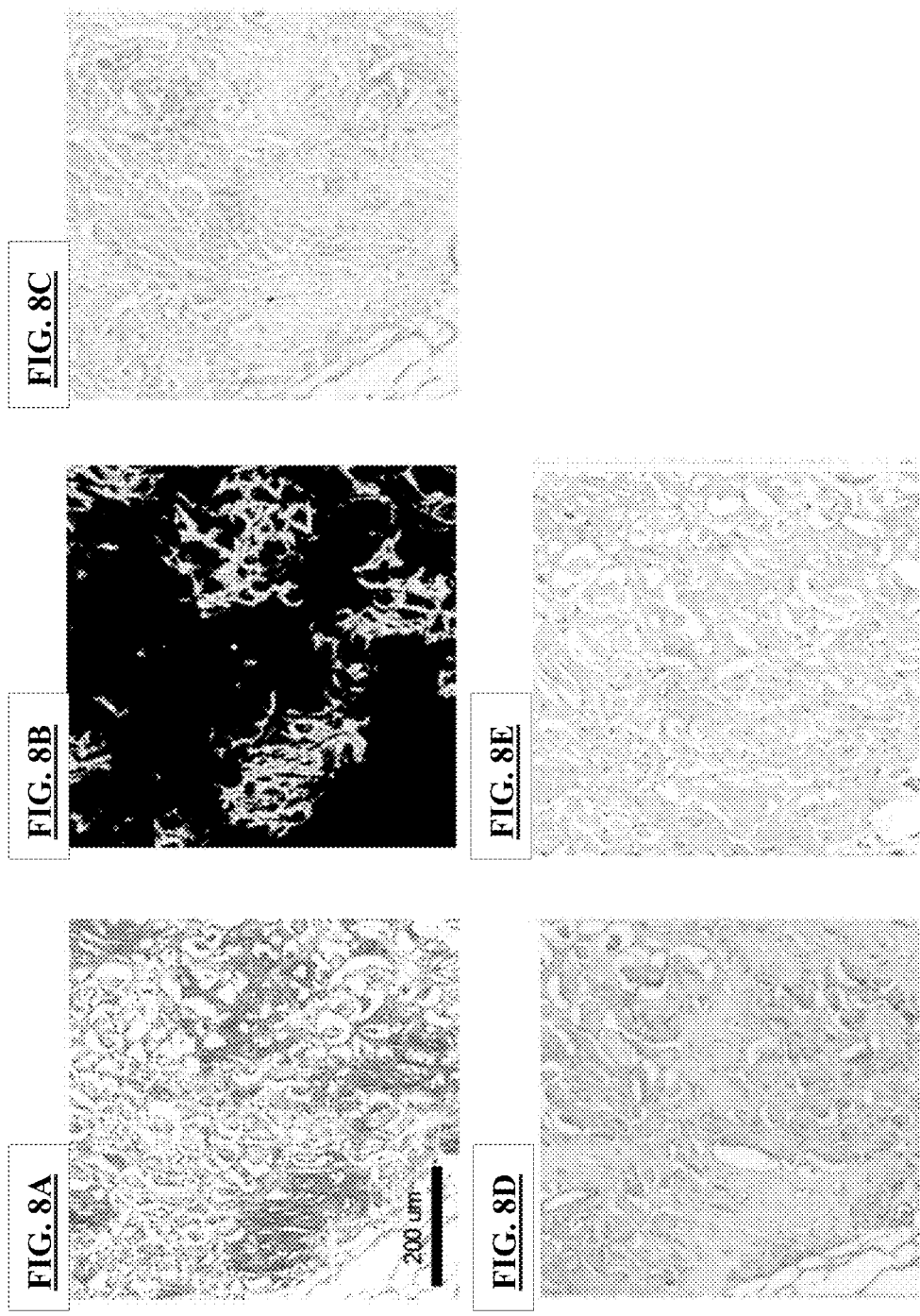

FIG. 10A

Heavy chain: Amino acid sequence (459 aa)

MECNWILPFILSVTSGVYSQVQLQQPGAELARPGASVKLSCKASGYTFTWIKQRPGQGLEWIGKATLTADESSSTAYMQLSSLASED
SAIYYCAIWGQGTTLTVSSAKTTPPSVYPLAPGSAAQTNSMVTLGCLVKGYFPEPVTVTWNSGSLSSGVHTFPAVLQSDLYTLSSSV
TVPSSTWPSETVTCNVAHPASSTKVDKKIVPRDCGCKPCICTVPEVSSVFIFPPKPKDVLTITLTPKVTCVVVDISKDDPEVQFSWF
VDDVEVHTAQTQPREEQFNSTFRSVSELPIMHQDWLNGKEFKCRVNSAAFPAPIEKTISKTKGRPKAPQVYTIPPPKEQMAKDKVSL
TCMITDFFPEDITVEWQWNGQPAENYKNTQPIMDTDGSYFVYSKLNVQKSNWEAGNTFTCSVLHEGLHNHHTEKSLSHSPGK-
(SEQ ID NO: 18)

FIG. 10B

Light chain: Amino acid sequence (238 aa)

MSPAQFLFLLVLWIRETNGDVVMTQTPLTLSVTVGQPASISCWLLQRPGQSPKRLIYGVPDRFTGSGSGTDFTLKISRVEAEDLGIY
YCFGGGTKLEIKRADAAPTVSIFPPSSEQLTSGGASVVCFLNNFYPKDINVKWKIDGSERQNGVLNSWTDQDSKDSTYSMSSTLLLT
KDEYERHNSYTCEATHKTSTSPIVKSFNRNEC-    (SEQ ID NO: 19)

Legend:

Signal peptide--FR1--FR2--FR3--FR4--Constant region--Stop codon

FIG. 10C

LX-96 Heavy chain DNA sequence (1380 bp)

ATGGAATGTAACTGGGGGCTGGATACTTCCTTTATTCTGTCAGTGGTCTCTACTCACAGGTTCAGCTGCAGCCTGGGGCTGAGCT
GGCAAGAGACCTGGAGTCTCAGTGAAGGTTGTCCTGCAAGGCTTCTGGCTACACCTTTACTTGGATAAAACAGAGGCCTGGACAGGGGTCTGG
AATGGATTGGGAAGGCCACATTGACTGCAGATGAATCCTGACACAGCCTACACTGCAGCTTGGCATCTGAGGACTCTGCG
ATCTATTACTGTGCAAGATCTGGGGCCAAGGCACCACTCTCACAGTCTCCTCAGCCAAACGACACCCCCATCTGTCTATCCACTGGCCCC
TGGATCTGCTGCCCAAACTAACTCCATGGTGACCCTGGGTCAAGGGCTATTTCCCTGAGCCAGTGACAGTGACCTGGAACT
CTGGATCCCCTGTCCAGCGGGTGTGCACACCTTCCCAGCTGTCCTGCAGTCGTGTCCTGCTCCTACACTCTGAGCAGCTCTGAGCCTGTCCCCTCC
AGCACCTGGCCAGTCCGTCACCTGCAACGTTGCCCACCCGGCCAGCGACACCCAAGGTGGACAAGAAAATTGTGCCCAGGGATTG
TGGTTGTAAGCCTTGCAGCATATGTGGGTAGACAGTCCCAGAAGTATCATCAGCAAGGATGATCCCGAGGTCCAGCTCACCATTACTC
TGACTCCTAAGGTCACGTGTGTTGTGGGGTAGACATCAGCAAGGATGACACTTCAGCTGGTTTGTAGATGATGTGGAGGTG
CACACAGCTCAGACGCACCCGGGAGGAGGCAGTTCAACAGCACTTTCCCTGCCCCATCATGCCACCAGGACTGGCT
CAATGGCAAGGAGGTTCAAATGCAGGGTCAACAGTGCAGCTTTCCCTGCCCCAAGATAAAGTCAGTCGAGAAAACCATCTCCAAAACCATCTCCAAAACCAGGCAGACCGA
AGGCTCCACAGGTGTACACCATTCCACCTCCCAAGGAGCAGGCAGTGGGCAGCGCCGGGAATGGGCCAGCGACAGTGGCAGTGGGGAACACTGGAGCCCATCATGGACACAGATGGCTC
TTACTTCGTCTACAGCCAGCTCAATGTGCAGAAGAGCAACTGGGAGGCAGGAAATACTTTCACCTGCTCTGTGTTACATGAGGGCCTGC
ACAACCACCATACTGAGAAGAGCCCTCTCTCCCACTCCTCCTGGTAAATGA (SEQ ID NO: 24)

FIG. 10D

LX-96 Light chain DNA sequence (717 bp)

ATGGAGTCCTGCCCAGTTCTCTGTTTCTGTTAGTGCTCTCTGGATTCGGGAAACAAATGGTGATGTTGTGATGACCCAGACTCCACTCACTTT
GTCGGTTACCGTTGGACAACCAGCCTCCATCTCTTGCTGTGTTGTTACAGAGGCCAGGGCCAGTCTCCAAAGCGCCTAATCTATGGAGTCC
CTGACAGGTTCACTGGCAGTGGATCAGGGACAGATTTCACACTAAAAATCAGCAGTGAGGCTGAGGATTTGGGAATTTATTATTGC
TTCGGTGGAGGCACCAAGCTGGAAATCAAACGGGCTGATGCTGCACCATCTGTATCCATCTTCCCACCATCAGTGAGCAGTTAACATC
TGGAGGTGCCTCAGTTCGTGTGCTTCTTGAACAACTTCTATCCCAGAACTCTCTTGAACAAGTGTCAAGTGGAAGGTGGATGGCCAGTTGAAGACAAA
ATGGGCGTCCTGAACAGTTGGACTGATCAGGACGAGCAAAGACAGCACCTACAGCCTCAGCACCATGGACGACGAGTAT
GAACGACATAACAGCTATACCTGTGAGGCCACTCACAGACATCAACTTCACCCATTGTCAAGAGCTTCAACAGGAATGAGTGTTAG
(SEQ ID NO: 25)

Legend:

Signal peptide–FR1––FR2––FR3––FR4–Constant region–Stop codon

A = Amyloid/end-stage diseased
M = Misfolded/early-stage diseased
N = Native/healthy light chains

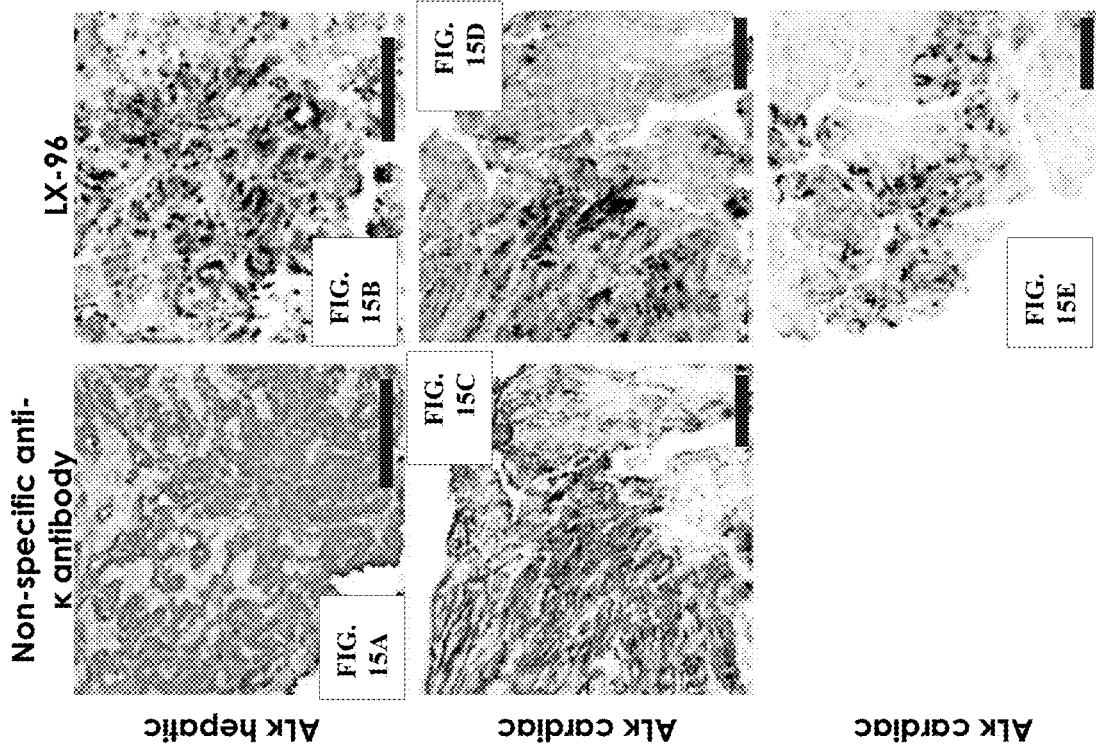

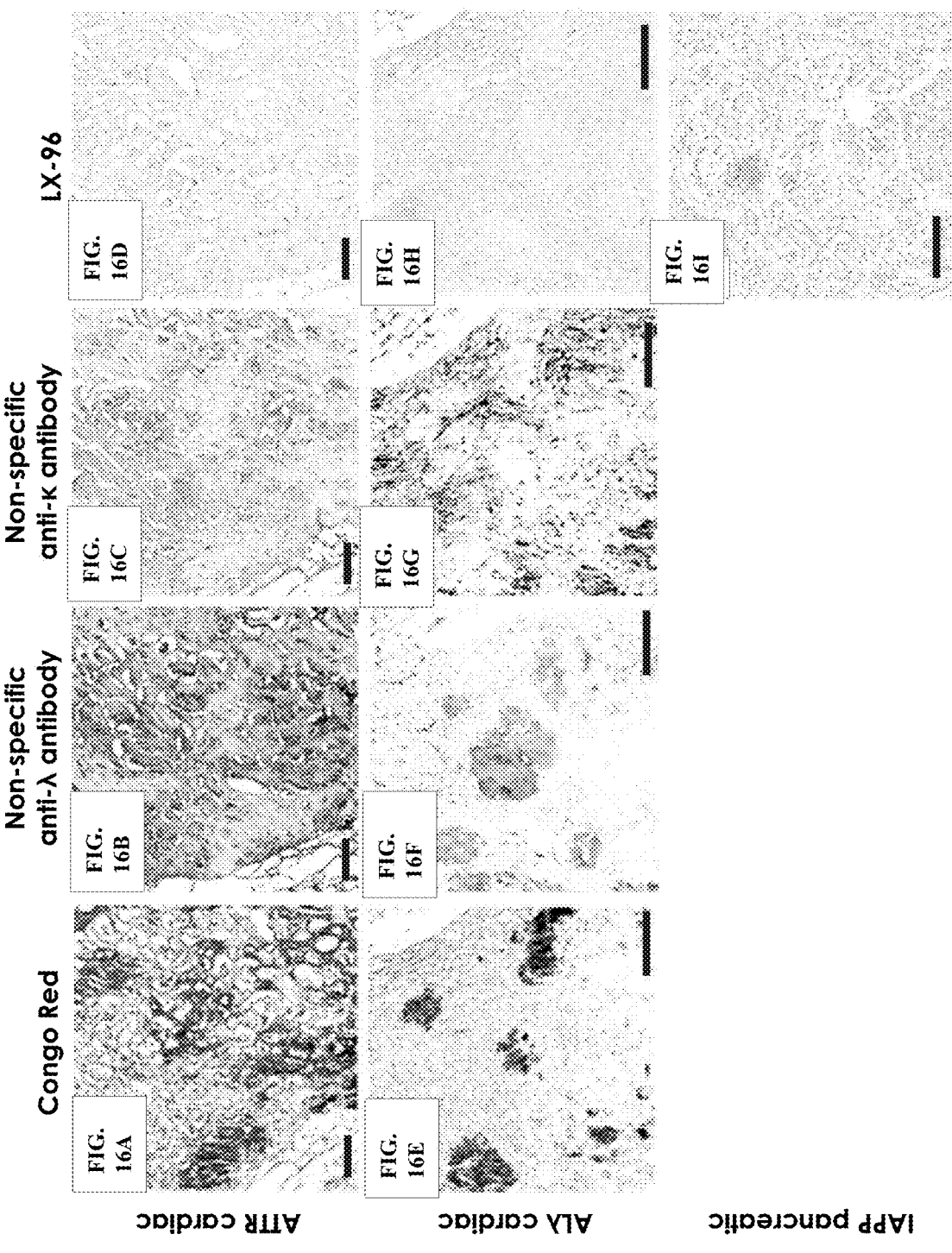

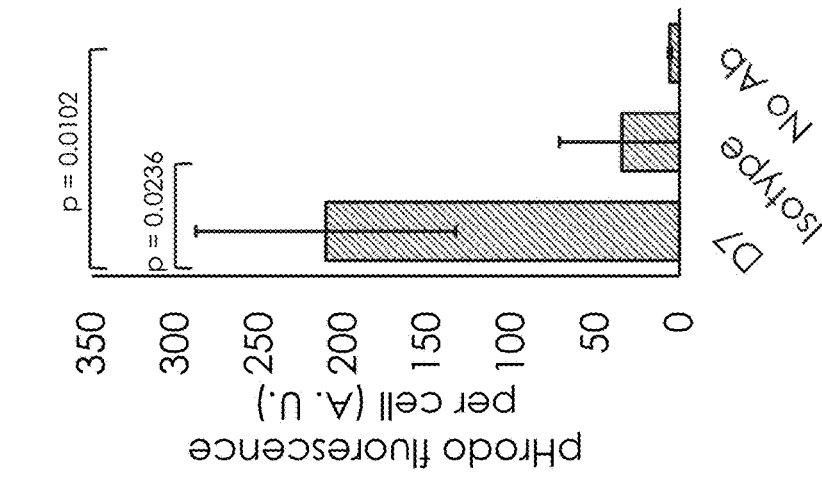
FIG. 18G
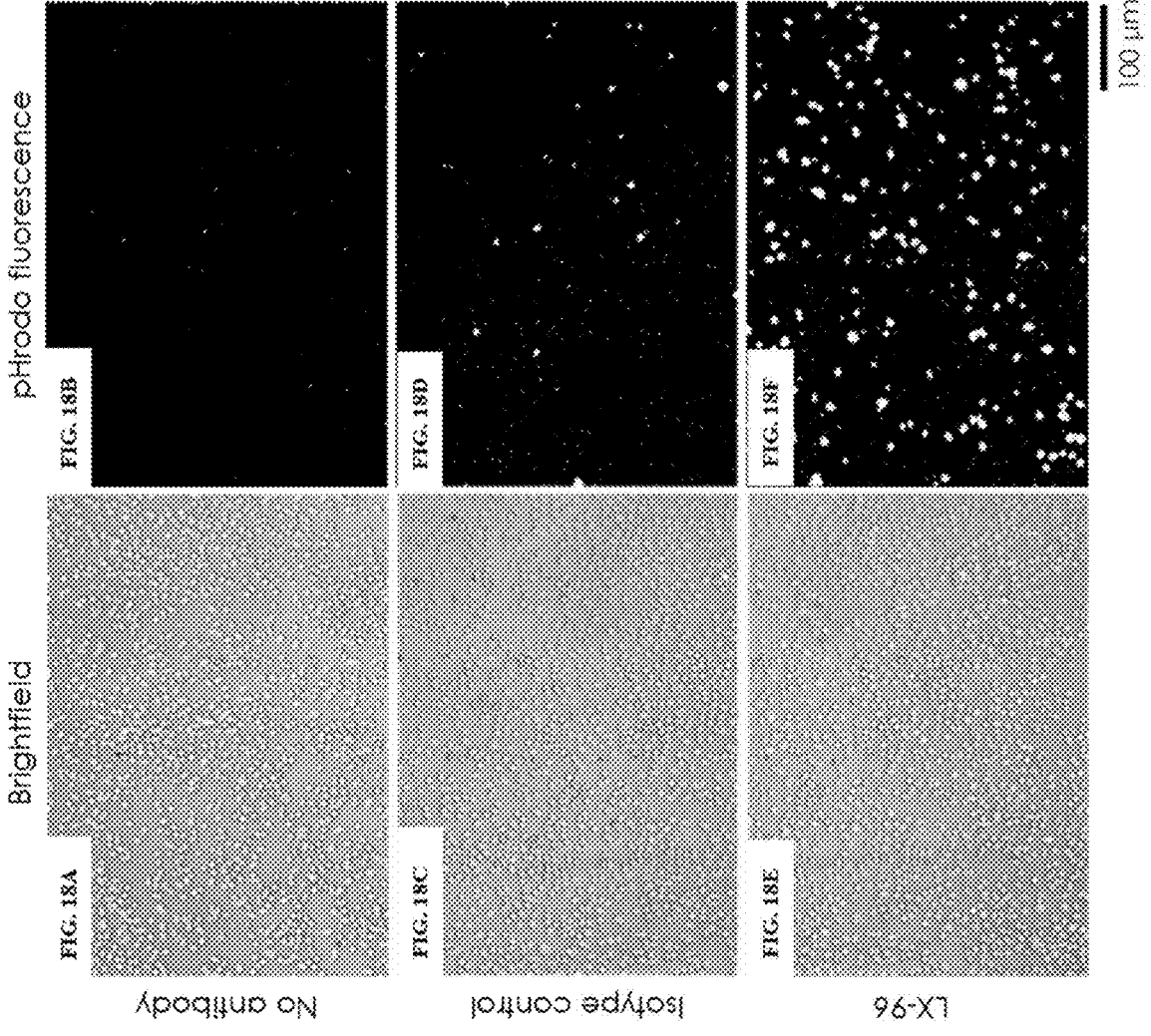

Normalized phagocytosis

Phagocytosis signal

FIG. 21C
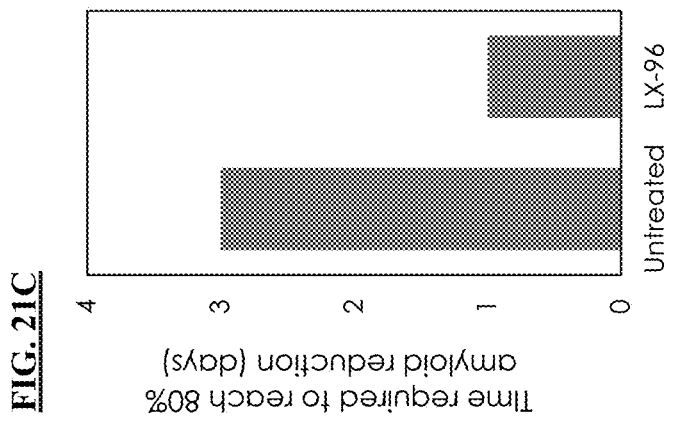
FIG. 21A
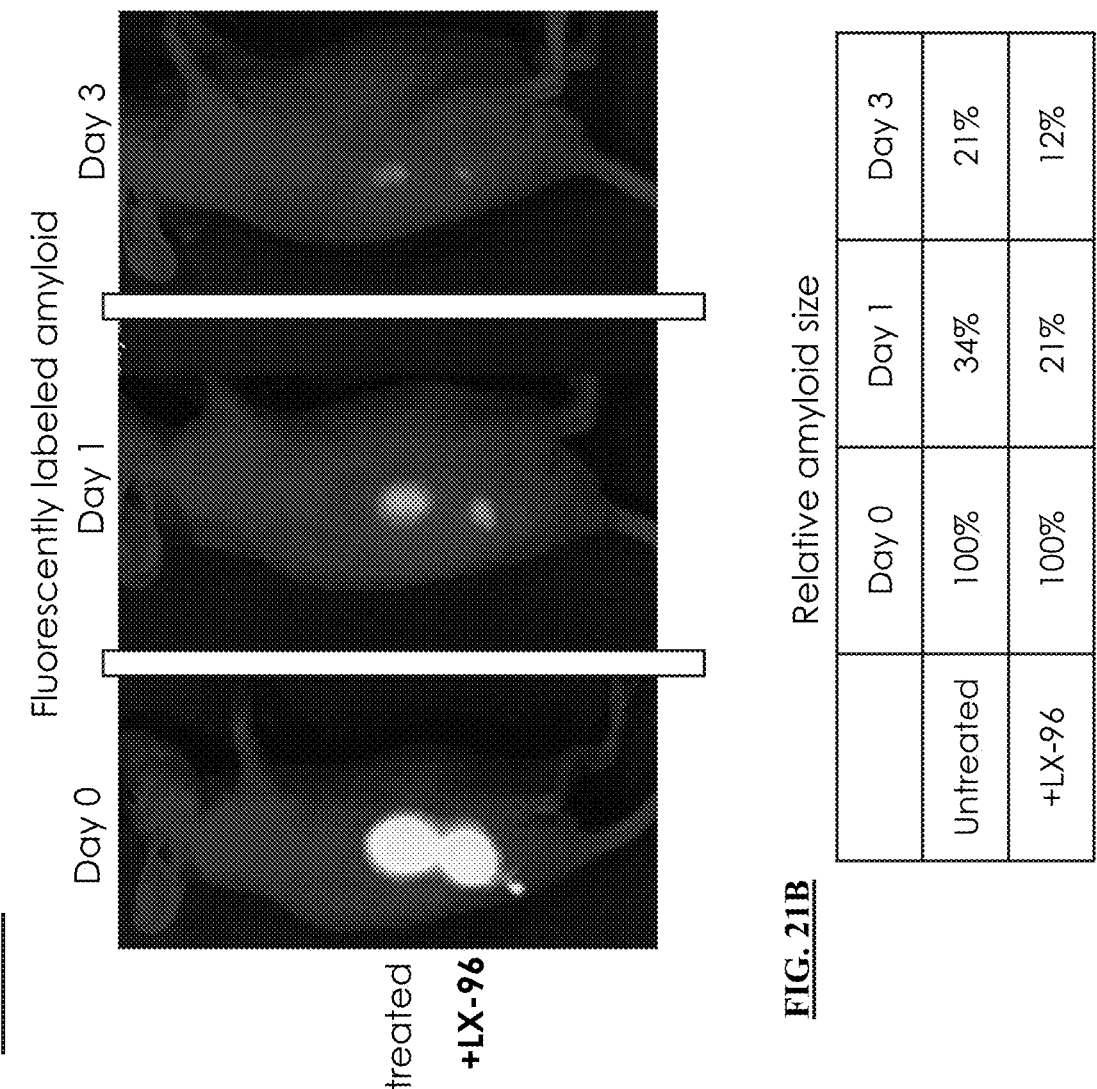
Fluorescently labeled amyloid
Day 0    Day 1    Day 3
Untreated
+LX-96
FIG. 21B
Relative amyloid size
| | Day 0 | Day 1 | Day 3 |
|---|---|---|---|
| Untreated | 100% | 34% | 21% |
| +LX-96 | 100% | 21% | 12% |

SEQUENCE LISTING

Sequence total quantity: 27
SEQ ID NO: 1          moltype = AA   length = 10
FEATURE               Location/Qualifiers
source                1..10
                      mol_type = protein
                      organism = Homo sapiens
SEQUENCE: 1
STYSLSSTLT                                                          10

SEQ ID NO: 2          moltype = AA   length = 11
FEATURE               Location/Qualifiers
source                1..11
                      mol_type = protein
                      organism = Homo sapiens
SEQUENCE: 2
NKYAASSYLS L                                                        11

SEQ ID NO: 3          moltype = AA   length = 18
FEATURE               Location/Qualifiers
REGION                1..18
                      note = Description of Artificial Sequence: Synthetic peptide
source                1..18
                      mol_type = protein
                      organism = synthetic construct
SEQUENCE: 3
GKGGSTYSLS STLTGGKG                                                 18

SEQ ID NO: 4          moltype = AA   length = 19
FEATURE               Location/Qualifiers
REGION                1..19
                      note = Description of Artificial Sequence: Synthetic peptide
source                1..19
                      mol_type = protein
                      organism = synthetic construct
SEQUENCE: 4
GKGGNKYAAS SYLSLGGKG                                                19

SEQ ID NO: 5          moltype = AA   length = 214
FEATURE               Location/Qualifiers
source                1..214
                      mol_type = protein
                      organism = Homo sapiens
SEQUENCE: 5
DIQMTQSPST LSASVGDRVT ITCRASQSIN TWLAWYQQKP GKAPKLLMYK ASSLESGVPS   60
RFIGSGSGTE FTLTISSLQP DDFATYYCQQ YNSDSKMFGQ GTKVEVKGTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 6          moltype = AA   length = 106
FEATURE               Location/Qualifiers
source                1..106
                      mol_type = protein
                      organism = Homo sapiens
SEQUENCE: 6
TVAAPSVFIF PPSDEQLKSG TASVVCLLNN FYPREAKVQW KVDNALQSGN SQESVTEQDS   60
KDSTYSLSST LTLSKADYEK HKVYACEVTH QGLSSPVTKS FNRGEC                  106

SEQ ID NO: 7          moltype = AA   length = 216
FEATURE               Location/Qualifiers
source                1..216
                      mol_type = protein
                      organism = Homo sapiens
SEQUENCE: 7
QSALTQPPSA SGSLGQSVTI SCTGTSSDVG GYNYVSWYQQ HAGKAPKVII YEVNKRPSGV   60
PDRFSGSKSG NTASLTVSGL QAEDEADYYC SSYEGSDNFV FGTGTKVTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                            216

SEQ ID NO: 8          moltype = AA   length = 105
FEATURE               Location/Qualifiers
source                1..105
                      mol_type = protein
                      organism = Homo sapiens
SEQUENCE: 8
QPKANPTVTL FPPSSEELQA NKATLVCLIS DFYPGAVTVA WKADGSPVKA GVETTKPSKQ   60
SNNKYAASSY LSLTPEQWKS HRSYSCQVTH EGSTVEKTVA PTECS                   105

SEQ ID NO: 9          moltype = AA   length = 16

```
FEATURE                Location/Qualifiers
REGION                 1..16
                       note = Description of Artificial Sequence: Synthetic peptide
source                 1..16
                       mol_type = protein
                       organism = synthetic construct
SEQUENCE: 9
CGGNKYAASS YLSLGG                                                      16

SEQ ID NO: 10          moltype = AA  length = 112
FEATURE                Location/Qualifiers
REGION                 1..112
                       note = Description of Artificial Sequence: Synthetic
                        polypeptide
source                 1..112
                       mol_type = protein
                       organism = synthetic construct
SEQUENCE: 10
DVVMTQTPLT LSVTVGQPAS ISCKSSQSLL DGDGKTYLNW LLQRPGQSPK RLIYLVSKLD  60
SGVPDRFTGS GSGTDFTLKI SRVEAEDLGI YYCWQGTHFP QTFGGGTKLE IK          112

SEQ ID NO: 11          moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 11
KSSQSLLDGD GKTYLN                                                      16

SEQ ID NO: 12          moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 12
LVSKLDS                                                                7

SEQ ID NO: 13          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 13
WQGTHFPQT                                                              9

SEQ ID NO: 14          moltype = AA  length = 116
FEATURE                Location/Qualifiers
REGION                 1..116
                       note = Description of Artificial Sequence: Synthetic
                        polypeptide
source                 1..116
                       mol_type = protein
                       organism = synthetic construct
SEQUENCE: 14
QVQLQQPGAE LARPGASVKL SCKASGYTFT SFWIQWIKQR PGQGLEWIGS IYPGDGDTRY  60
IQKFRGKATL TADESSSTAY MQLSSLASED SAIYYCAIVT TAPDYWGQGT TLTVSS      116

SEQ ID NO: 15          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 15
SFWIQ                                                                  5

SEQ ID NO: 16          moltype = AA  length = 17
FEATURE                Location/Qualifiers
REGION                 1..17
                       note = Description of Artificial Sequence: Synthetic peptide
source                 1..17
                       mol_type = protein
```

-continued

```
                        organism = synthetic construct
SEQUENCE: 16
SIYPGDGDTR YIQKFRG                                              17

SEQ ID NO: 17           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 17
VTTAPDY                                                         7

SEQ ID NO: 18           moltype = AA  length = 430
FEATURE                 Location/Qualifiers
REGION                  1..430
                        note = Description of Artificial Sequence: Synthetic
                         polypeptide
source                  1..430
                        mol_type = protein
                        organism = synthetic construct
SEQUENCE: 18
MECNWILPFI LSVTSGVYSQ VQLQQPGAEL ARPGASVKLS CKASGYTFTW IKQRPGQGLE  60
WIGKATLTAD ESSSTAYMQL SSLASEDSAI YYCAIWGQGT TLTVSSAKTT PPSVYPLAPG  120
SAAQTNSMVT LGCLVKGYFP EPVTVTWNSG SLSSGVHTFP AVLQSDLYTL SSSVTVPSST  180
WPSETVTCNV AHPASSTKVD KKIVPRDCGC KPCICTVPEV SSVFIFPPKP KDVLTITLTP  240
KVTCVVVDIS KDDPEVQFSW FVDDVEVHTA QTQPREEQFN STFRSVSELP IMHQDWLNGK  300
EFKCRVNSAA FPAPIEKTIS KTKGRPKAPQ VYTIPPPKEQ MAKDKVSLTC MITDFFPEDI  360
TVEWQWNGQP AENYKNTQPI MDTDGSYFVY SKLNVQKSNW EAGNTFTCSV LHEGLHNHHT  420
EKSLSHSPGK                                                      430

SEQ ID NO: 19           moltype = AA  length = 206
FEATURE                 Location/Qualifiers
REGION                  1..206
                        note = Description of Artificial Sequence: Synthetic
                         polypeptide
source                  1..206
                        mol_type = protein
                        organism = synthetic construct
SEQUENCE: 19
MSPAQFLFLL VLWIRETNGD VVMTQTPLTL SVTVGQPASI SCWLLQRPGQ SPKRLIYGVP  60
DRFTGSGSGT DFTLKISRVE AEDLGIYYCF GGGTKLEIKR ADAAPTVSIF PPSSEQLTSG  120
GASVVCFLNN FYPKDINVKW KIDGSERQNG VLNSWTDQDS KDSTYSMSST LTLTKDEYER  180
HNSYTCEATH KTSTSPIVKS FNRNEC                                    206

SEQ ID NO: 20           moltype =   length =
SEQUENCE: 20
000

SEQ ID NO: 21           moltype =   length =
SEQUENCE: 21
000

SEQ ID NO: 22           moltype =   length =
SEQUENCE: 22
000

SEQ ID NO: 23           moltype =   length =
SEQUENCE: 23
000

SEQ ID NO: 24           moltype = DNA  length = 1293
FEATURE                 Location/Qualifiers
misc_feature            1..1293
                        note = Description of Artificial Sequence: Synthetic
                         polynucleotide
source                  1..1293
                        mol_type = other DNA
                        organism = synthetic construct
SEQUENCE: 24
atggaatgta actggatact tcctttttatt ctgtcagtaa cttcaggtgt ctactcacag  60
gttcagctca agcagcctgg ggctgagctg gcaagacctg gggcttcagt gaagttgtcc  120
tgcaaggctt ctggctacac ctttacttgg ataaaacaga ggcctggaca gggtctggaa  180
tggattggga aggccacatt gactgcagat gaatcctcca gcacagccta catgcagctc  240
agcagcttgg catctgagga ctctgcgatc tattactgtg caatctgggg ccaaggcacc  300
actctcacag tctcctcagc caaaacgaca ccccccatctg tctatccact ggcccctgga  360
tctgctgccc aaactaactc catggtgacc ctggatgcc tggtcaaggg ctatttccct  420
gagccagtga cagtgacctg gaactctgga tccctgtcca gcggtgtgca caccttccca  480
```

-continued

```
gctgtcctgc agtctgacct ctacactctg agcagctcag tgactgtccc ctccagcacc    540
tggcccagcg agaccgtcac ctgcaacgtt gcccacccgg ccagcagcac caaggtggac    600
aagaaaattg tgcccaggga ttgtggttgt aagccttgca tatgtacagt cccagaagta    660
tcatctgtct tcatcttccc cccaaagccc aaggatgtgc tcaccattac tctgactcct    720
aaggtcacgt gtgttgtggt agacatcagc aaggatgatc ccgaggtcca gttcagctgg    780
tttgtagatg atgtggaggt gcacacagct cagacgcaac cccgggagga gcagttcaac    840
agcactttcc gctcagtcag tgaacttccc atcatgcacc aggactggct caatggcaag    900
gagttcaaat gcagggtcaa cagtgcagct ttccctgccc ccatcgagaa aaccatctcc    960
aaaaccaaag gcagaccgaa ggctccacag gtgtacacca ttccacctcc caaggagcag   1020
atggccaagg ataaagtcag tctgacctgc atgataacag acttcttccc tgaagacatt   1080
actgtggagt ggcagtggaa tgggcagcca gcggagaact acaagaacac tcagcccatc   1140
atggacacag atggctctta cttcgtctac agcaagctca atgtgcagaa gagcaactgg   1200
gaggcaggaa atactttcac ctgctctgtg ttacatgagg gcctgcacaa ccaccatact   1260
gagaagagcc tctcccactc tcctggtaaa tga                                1293
```

```
SEQ ID NO: 25              moltype = DNA  length = 621
FEATURE                    Location/Qualifiers
misc_feature               1..621
                           note = Description of Artificial Sequence: Synthetic
                            polynucleotide
source                     1..621
                           mol_type = other DNA
                           organism = synthetic construct
SEQUENCE: 25
atgagtcctg cccagttcct gtttctgtta gtgctctgga ttcgggaaac aaatggtgat    60
gttgtgatga cccagactcc actcactttg tcggttcacg ttggacaacc agcctccatc   120
tcttgctggt tgttacagag gccaggccag tctccaaagc gcctaatcta tggagtccct   180
gacaggttca ctggcagtgg atcagggaca gatttcacac taaaaatcag cagagtggag   240
gctgaggatt tgggaattta ttattgcttc ggtggaggca ccaagctgga aatcaaacgg   300
gctgatgctg caccaactgt atccatcttc ccaccatcca gtgagcagtt aacatctgga   360
ggtgcctcag tcgtgtgctt cttgaacaac ttctacccca aagacatcaa tgtcaagtgg   420
aagattgatg gcagtgaacg acaaaatggc gtcctgaaca gttggactga tcaggacagc   480
aaagacagca cctacagcat gagcagcacc ctcacgttga ccaaggacga gtatgaacga   540
cataacagct atacctgtga ggccactcac aagacatcaa cttcacccat tgtcaagagc   600
ttcaacagga atgagtgtta g                                             621
```

```
SEQ ID NO: 26              moltype = AA  length = 15
FEATURE                    Location/Qualifiers
REGION                     1..15
                           note = Description of Artificial Sequence: Synthetic peptide
source                     1..15
                           mol_type = protein
                           organism = synthetic construct
SEQUENCE: 26
GGGGSGGGGS GGGGS                                                     15
```

```
SEQ ID NO: 27              moltype = AA  length = 19
FEATURE                    Location/Qualifiers
REGION                     1..19
                           note = Description of Artificial Sequence: Synthetic peptide
source                     1..19
                           mol_type = protein
                           organism = synthetic construct
SEQUENCE: 27
CGKGGSTYSL SSTLTGGKG                                                 19
```

IMMUNOGLOBULIN LIGHT CHAIN ANTIBODIES AND USES THEREOF

CROSS REFERENCE TO RELATED APPLICATIONS

This Application is Continuation of International Application No. PCT/IB2021/000897, filed on Dec. 13, 2021, which claims the benefit of U.S. Provisional Application No. 63/125,281 filed on Dec. 14, 2020, both of which are incorporated by reference herein in its entirety.

SEQUENCE LISTING

The instant application contains a Sequence Listing which has been submitted electronically in XML format and is hereby incorporated by reference in its entirety. The XML copy, created on Oct. 14, 2023, is named 60070701601_sl.xml and is 32,135 bytes in size.

BACKGROUND OF THE DISCLOSURE

AL amyloidosis is a widely underdiagnosed disease caused by the misfolding of free immunoglobulin light chains (LC) which can deposit as light chain amyloid (AL) in the heart, kidneys, or liver. The condition is caused by an underlying plasma cell dyscrasia that results in plasma cells secreting a large excess of free immunoglobulin kappa (κ) and/or lambda (λ) light chains into circulation. Disease is caused by the deposition of a unique light chain secreted by a single clonal plasma cell population.

However, little is known about the origins of AL. Thus, there is a critical need to develop tools that will uncover the underlying mechanism of AL formation for the design of optimal therapeutics.

SUMMARY OF THE DISCLOSURE

Described herein are certain epitopes of human light chains and antibodies that bind said epitopes. The epitopes described herein are advantageous because they allow the production and/or screening of antibodies that bind to and promote the clearance of misfolded light chains, which are the etiological agent of light chain amyloidosis. One obstacle to the treatment of light chain amyloidosis is that different patients may produce light chains with different amino acid sequences that are not bound equally well by current anti-light chain antibodies that target variable regions. The antibodies described herein target epitopes in the constant regions of kappa and lambda light chains, and, thus, allow for more consistent clinical results and less patient-to-patient variability in outcome. The universality of binding also allows for the additional benefit to using the disclosed antibodies as a part of a diagnostic test for light chain amyloidosis. Additionally, the antibodies described herein are specific for misfolded light chains and have little reactivity to properly folded light chains, thus reducing the chances of unwanted immunological side-effects attributable to reduce antibody levels.

Certain aspects of the present disclosure are directed to an antibody that specifically binds human free immunoglobulin light chain (FLC; "anti-FLC antibody"), wherein the anti-FLC antibody cross competes with a reference antibody for binding to kappa light chain, wherein the reference antibody binds an epitope on immunoglobulin kappa light chain comprising or consisting of the amino acid sequence set forth in STYSLSSTLT (SEQ ID NO: 1). In some aspects, the antibody binds kappa light chain at an epitope that overlaps all or a portion of the amino acid sequence set forth in STYSLSSTLT (SEQ ID NO: 1). In some aspects, the antibody binds an epitope on kappa light chain comprising or consisting of the amino acid sequence set forth in STYS-LSSTLT (SEQ ID NO: 1).

Certain aspects of the present disclosure are directed to an antibody that specifically binds human free immunoglobulin light chain ("anti-FLC antibody"), wherein the anti-FLC antibody cross competes with a reference antibody for binding to lambda light chain, wherein the reference antibody binds an epitope on immunoglobulin lambda light chain comprising or consisting of the amino acid sequence set forth in NKYAASSYLSL (SEQ ID NO: 2). In some aspects, the antibody binds lambda light chain at an epitope that overlaps with the amino acid sequence set forth in NKYAASSYLSL (SEQ ID NO: 2). In some aspects, the antibody binds an epitope on lambda light chain comprising or consisting of the amino acid sequence set forth in NKYAASSYLSL (SEQ ID NO: 2).

In some aspects, the antibody does not bind a complex comprising immunoglobulin light chain covalently linked to immunoglobulin heavy chain. In some aspects, the FLC comprises an aggregate of immunoglobulin light chain peptides. In some aspects, the aggregate of immunoglobulin light chain peptides comprises one or more misfolded immunoglobulin light chain peptides.

In some aspects, the antibody binds light chain amyloid fibrils. In some aspects, the amyloid fibrils are collected from a biological sample obtained from a subject. In some aspects, the biological sample is selected from blood, serum, plasma, solid tissue, and any combination thereof.

In some aspects, the FLC comprises a fragment of an immunoglobulin light chain peptide. In some aspects, the FLC comprises a full length immunoglobulin light chain peptide. In some aspects, the antibody is a polyclonal antibody or a monoclonal antibody. In some aspects, the antibody is a chimeric antibody, a humanized antibody, or human antibody. In some aspects, the antibody comprises an antigen-binding portion of an antibody selected from the group consisting of a Fab, Fab', F(ab')2, scFv, dsFv, ds-scFv, dimer, minibody, diabody, a multimer thereof, and a bispecific antibody fragment. In some aspects, the antibody is a single chain antibody.

In some aspects, the antibody is fused to or associated with a label. In some aspects, the label comprises a chemical label, a biological label, a fluorescent label, or any combination thereof.

In some aspects, the antibody comprises a heavy chain and a light chain. In some aspects, the antibody comprises a heavy chain variable region and a light chain variable region. In some aspects, the heavy chain variable region comprises a variable heavy complementarity determining region (VH-CDR) 1, a VH-CDR2, and a VH-CDR3, wherein: (a) the VH-CDR1 comprises the amino acid sequence set forth in SEQ ID NO: 15; (b) the VH-CDR1 comprises the amino acid sequence set forth in SEQ ID NO: 16; (c) the VH-CDR1 comprises the amino acid sequence set forth in SEQ ID NO: 17; or (d) any combination of (a)-(c). In some aspects, the heavy chain variable region comprises a VH-CDR1, a VH-CDR2, and a VH-CDR3, wherein: (a) the VH-CDR1 comprises the amino acid sequence set forth in SEQ ID NO: 15; (b) the VH-CDR1 comprises the amino acid sequence set forth in SEQ ID NO: 16; and (c) the VH-CDR1 comprises the amino acid sequence set forth in SEQ ID NO: 17. In some aspects, the light chain variable region comprises a variable light complementarity determining region (VL-CDR) 1, a VL-CDR2, and a VL-CDR3, wherein: (a) the VL-CDR1 comprises the amino acid sequence set forth in SEQ ID NO: 11; (b) the VL-CDR1 comprises the amino acid sequence set forth in SEQ ID NO: 12; (c) the VL-CDR1 comprises the amino acid sequence set forth in SEQ ID NO: 13; or (d) any combination of (a)-(c). In some aspects, the light chain variable region comprises a VL-CDR1, a VL-CDR2, and a VL-CDR3, wherein: (a) the VL-CDR1 comprises the amino acid sequence set forth in SEQ ID NO: 11; (b) the VL-CDR1 comprises the amino acid sequence set forth in SEQ ID NO: 12; and (c) the VL-CDR1 comprises the amino acid sequence set forth in SEQ ID NO: 13.

In some aspects, the antibody comprises: (a) a VL-CDR1 comprising the amino acid sequence set forth in SEQ ID NO: 11; (b) a VL-CDR2 comprising the amino acid sequence set forth in SEQ ID NO: 12; (c) a VL-CDR3 comprising the amino acid sequence set forth in SEQ ID NO: 13; (d) a VH-CDR1 comprising the amino acid sequence set forth in SEQ ID NO: 15; (e) a VH-CDR2 comprising the amino acid sequence set forth in SEQ ID NO: 16; and (f) a VH-CDR3 comprising the amino acid sequence set forth in SEQ ID NO: 17.

In some aspects, the antibody comprises a heavy chain variable region comprising the amino acid sequence set forth in SEQ ID NO: 14. In some aspects, the antibody comprises a light chain variable region comprising the amino acid sequence set forth in SEQ ID NO: 10. In some aspects, the antibody comprises a heavy chain variable region comprising the amino acid sequence set forth in SEQ ID NO: 14 and a light chain variable region comprising the amino acid sequence set forth in SEQ ID NO: 10.

Certain aspects of the present disclosure are directed to a polynucleotide or a set of polynucleotides encoding an antibody disclosed herein. Certain aspects of the present disclosure are directed to a vector or a set of vectors comprising a polynucleotide or a set of polynucleotides disclosed herein. In some aspects, the vector further comprises one or more regulatory elements.

Certain aspects of the present disclosure are directed to a host cell comprising an antibody disclosed herein, a polynucleotide or a set of polynucleotides disclosed herein, or a vector or a set of vectors disclosed herein.

Certain aspects of the present disclosure are directed to a pharmaceutical composition comprising an antibody disclosed herein, a polynucleotide or a set of polynucleotides disclosed herein, a vector or a set of vectors disclosed herein, or a host cell disclosed herein; and a pharmaceutically acceptable excipient.

Certain aspects of the present disclosure are directed to a method of making an antibody that specifically binds FLC, comprising culturing a host cell disclosed herein under suitable conditions. In some aspects, the method further comprises isolating the antibody.

Certain aspects of the present disclosure are directed to a method of diagnosing AL mediated amyloidosis comprising contacting a biological sample obtained from a subject with an antibody disclosed herein.

Certain aspects of the present disclosure are directed to a method of measuring FLC in a biological sample obtained from a subject, comprising contacting the biological sample with an antibody disclosed herein.

In some aspects, the subject has one or more amyloid deposit. In some aspects, the subject is afflicted with a disease or condition characterized by an amyloid deposit. In some aspects, the biological sample is selected from blood, serum, plasma, solid tissue, and any combination thereof.

Certain aspects of the present disclosure are directed to a method of treating a subject having one or more amyloid deposit, comprising administering to the subject a therapeutically effective amount of an antibody disclosed herein.

Certain aspects of the present disclosure are directed to a method of treating a subject having a disease or condition characterized by an amyloid deposit comprising administering to the subject a therapeutically effective amount of an antibody disclosed herein.

In some aspects, the subject has a plasma cell disorder. In some aspects, the subject has a systemic amyloidosis. In some aspects, the subject has AL amyloidosis.

Certain aspects of the present disclosure are directed to a method of treating a plasma cell disorder in a subject in need thereof, comprising administering to the subject a therapeutically effective amount of an antibody disclosed herein.

In some aspects, the plasma cell disorder comprises plasma cell dyscrasias. In some aspects, the plasma cell dyscrasias is selected from a monoclonal gammopathy of unknown significance (MGUS), multiple myeloma (MM), plasma cell leukemia (PCL), and any combination thereof.

Certain aspects of the present disclosure are directed to a method of treating a systemic amyloidosis in a subject in need thereof, comprising administering to the subject a therapeutically effective amount of an antibody disclosed herein. In some aspects, the systemic amyloidosis comprises AL amyloidosis.

In some aspects, the anti-FLC antibody reduces the size of at least one amyloid deposit in the subject relative to the size of the at least one amyloid deposit in the subject prior to the administering. In some aspects, the anti-FLC antibody reduces the number of amyloid deposits in the subject relative to the number of amyloid deposits in the subject prior to the administering. In some aspects, the anti-FLC antibody reduces the rate of amyloid deposit formation in the subject relative to the rate of amyloid deposit formation in the subject prior to the administering. In some aspects, the anti-FLC antibody halts the rate of amyloid deposit formation in the subject relative to the rate of amyloid deposit formation in the subject prior to the administering.

In some aspects disclosed herein is a method of making, screening for, or selecting an antibody directed to a kappa light chain constant region comprising contacting an antibody producing cell or a conditioned media thereof, a polyclonal antibody mixture, or a phage display library to a polypeptide comprising the sequence of SEQ ID NO:1. In certain embodiments, the antibody producing cell is a hybridoma. In certain embodiments, the polypeptide is less than 50 amino acids in length. In certain embodiments, the polypeptide is less than 25 amino acids in length. In certain embodiments, the polypeptide comprises a first portion and a second portion, wherein the first portion consists of the sequence of SEQ ID NO: 1, and the second portion comprises an amino acid sequence heterologous to a kappa light chain constant region. In certain embodiments, the polypeptide consists of SEQ ID NO: 1. In certain embodiments, the method further comprises selecting an antibody that binds to SEQ ID NO: 1.

In some aspects disclosed herein is a method of making, screening for, or selecting an antibody directed to a lambda light chain constant region comprising contacting an antibody producing cell or a conditioned media thereof, an antibody mixture, or a phage display library to a polypeptide comprising the sequence of SEQ ID NO:2. In certain embodiments, the antibody producing cell is a hybridoma. In certain embodiments, the polypeptide is less than 50 amino acids in length. In certain embodiments, the polypeptide is less than 25 amino acids in length. In certain embodiments, the polypeptide comprises a first portion and a second portion, wherein the first portion consists of the sequence of SEQ ID NO: 2, and the second portion comprises an amino acid sequence heterologous to a lambda light chain constant region. In certain embodiments, the polypeptide consists of SEQ ID NO: 2. In certain embodiments, the method further comprises selecting an antibody that binds to SEQ ID NO: 2.

BRIEF DESCRIPTION OF THE DRAWINGS

FIGS. 1A-1B are schematic illustrations of the pathology-specific epitope present in both κ and λ constant domain ($C_L$) regions of full length FL-LC. FIG. 1A shows the pathology-specific $C_L$ epitope is a buried epitope within the normal, natively-folded FL-LC homodimer, but exposed in AL amyloidosis. FIG. 1B shows the pathology-specific $C_L$ epitope is exposed in amyloidogenic misfolding intermediates during the FL-LC amyloid (FL-AL) formation pathway, which can be captured using antibodies.

FIG. 3A is a western blot showing that a κ light chain isotype rabbit polyclonal antibody disclosed herein shows specificity for kappa light chains and not lambda light chains. FIG. 3B is a western blot showing that commercial antibodies have specificity for their designated isotypes, and a secondary antibody only shows no binding.

FIGS. 5A-5C are images from immunogold electron microscopy using a κ light chain isotype rabbit polyclonal antibody showing binding to kappa light chain aggregates. FIG. 5A depicts the results of an assay performed with a κ light chain isotype rabbit polyclonal antibody on aggregates prepared at pH 4.5 and shows binding to large aggregates approximately 100 nm in size. FIGS. 5B and 5C depict the results of an assay performed with a κ light chain isotype rabbit polyclonal antibody on aggregates prepared at pH 6 and show binding to large aggregates approximately 75 nm in size.

FIGS. 6A-6B are scatter plots showing that the κ light chain isotype rabbit polyclonal antibody enhances uptake of kappa light chain aggregates by THP-1 monocyte cells. Monocytes phagocytosed pHrodo-labelled aggregates approximately 3 times more frequently in the presence of κ light chain isotype rabbit polyclonal antibody (FIG. 6B) compared to no antibody (FIG. 6A).

FIGS. 7A-7J show immunohistochemistry staining of cardiac tissue from a patient with lambda AL amyloidosis. Congo red staining (FIGS. 7A-7B), Congo red fluorescence (FIGS. 7C-7D), and DAKO anti-lambda antibody (FIGS. 7E-7F) all co-stain amyloid, suggesting a lambda light chain cardiac amyloidosis patient. DAKO anti-kappa (FIGS. 7G-7H) stains other regions of tissue, and the κ light chain isotype rabbit polyclonal antibody (FIGS. 8I-8J) shows little to no staining indicating it does not cross-react with lambda amyloid.

FIGS. 8A-8E show immunohistochemistry staining of cardiac tissue from an ATTR cardiac amyloid patient. Congo red staining (FIG. 8A) and Congo red fluorescence (FIG. 8B) indicate the presence of amyloid. The amyloid is not bound by DAKO anti-lamba antibody (FIG. 8C), DAKO anti-kappa antibody (FIG. 8D), or the κ light chain isotype rabbit polyclonal antibody (FIG. 8E).

FIGS. 10A-10D are amino acid (FIGS. 10A-10B) and nucleic acid (FIGS. 10C-10D) sequences for the LX-96 anti-kappa monoclonal antibody heavy chain (FIGS. 10A and 10C) and light chain (FIGS. 10B and 10D). The signal peptide sequences are in plain text.

FIG. 11C demonstrates LX-96 binding to detect native or misfolded forms of another kappa light chain variant AL12.

FIGS. 13A-13D).

FIGS. 15A-15E are images of immunohistochemistry staining of biopsy-confirmed cases of kappa AL amyloidosis. A hepatic (FIGS. 15A-15B) and two cardiac cases (FIGS. 15C-15E) were stained (dark regions) using either non-specific anti-kappa antibody (FIGS. 15A and 15C) or LX-96 (FIGS. 15B, 15D, and 15E). Scale bar=100 μm.

FIGS. 16A-16I are images of immunohistochemistry staining of biopsy-confirmed cases of amyloidosis as pathological control tissue. ATTR cardiac (FIGS. 16A-16D), AL-lambda cardiac (FIGS. 16E-16H), or IAPP pancreatic tissue (FIG. 16I) was stained using either Congo red (FIGS. 16A and 16E; dark stain), non-specific anti-lambda antibody (FIGS. 16B and 16F), non-specific anti-kappa antibody (FIGS. 16C and 16G) or LX-96 (FIGS. 16D, 16H, and 16I). Positive antibody staining appears as black. LX-96 showed no staining in any of these tissues. Scale bar=100 μm.

FIGS. 18A-18F are brightfield and epifluorescence images of RAW cells in representative fields of view with brightfield (FIGS. 18A, 18C and 18E) and pHrodo (FIGS. 18B, 18D and 18F) channels. Cells were incubated with pHrodo-labeled AL09 for 3 h in the presence of LX-96 (FIGS. 18E-18F), an isotype antibody (FIGS. 18C-18D) or in the absence of antibodies (FIGS. 18A, 18B) as controls. The pHrodo fluorescence signal (white) represents cells that have internalized AL09 amyloid via phagocytic uptake. FIG. 18G is a bar graph illustrating uptake as quantified by average pHrodo fluorescence per cell. p-values were calculated using student t-test.

FIG. 21A are fluorescence images of a mouse implanted with fluorescently labeled amyloidoma (top) or labeled amyloidoma pre-mixed with 10 mg/kg LX-96 (bottom). Images were taken over 3 days and the white signal infers amyloid size. FIG. 21B tabulates the relative size of the amyloid quantified by total fluorescence signal. FIG. 21C is a graph illustrating the enhanced speed (3-fold) of amyloid size reduction when LX-96 is administered compared to the untreated amyloidoma.

DETAILED DESCRIPTION OF THE DISCLOSURE

Figure 2B:
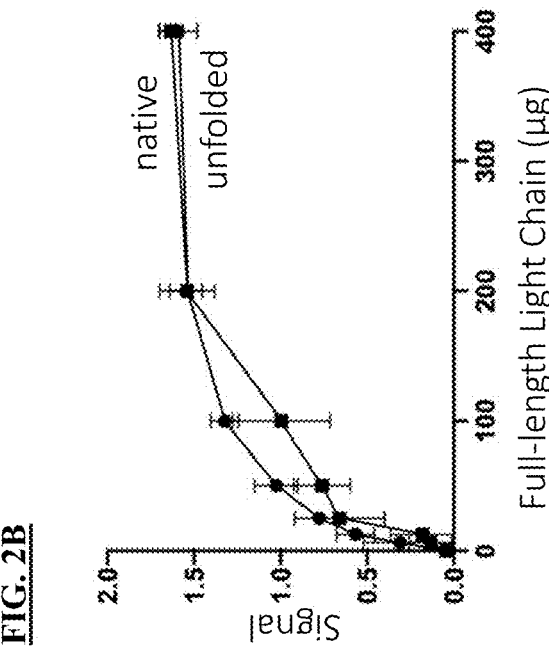
FIGS. 2A-2B are graphs showing the detection of native and unfolded full-length light chain proteins by indirect ELISA using a κ light chain isotype rabbit polyclonal antibody described herein (FIG. 2A) or a commercial pan-specific antibody (FIG. 2B).

Certain aspects of the present disclosure are directed to antibodies that specifically binds human free immunoglobulin light chain (FLC; "anti-FLC antibody"). In some aspects, the anti-FLC antibody binds a kappa light chain. In some aspects, the anti-FLC antibody cross competes with a reference antibody for binding to kappa light chain, wherein the reference antibody binds an epitope on immunoglobulin kappa light chain comprising the amino acid sequence set forth in STYSLSSTLT (SEQ ID NO: 1). In some aspects, the anti-FLC antibody binds kappa light chain at an epitope that overlaps all or a portion of the amino acid sequence set forth in STYSLSSTLT (SEQ ID NO: 1). In some aspects, the anti-FLC antibody binds an epitope on kappa light chain comprising the amino acid sequence set forth in STYS-LSSTLT (SEQ ID NO: 1).

In some aspects, the anti-FLC antibody binds a lambda light chain. In some aspects, the anti-FLC antibody cross competes with a reference antibody for binding to lambda light chain, wherein the reference antibody binds an epitope on immunoglobulin lambda light chain comprising the amino acid sequence set forth in NKYAASSYLSL (SEQ ID NO: 2). In some aspects, the anti-FLC antibody binds lambda light chain at an epitope that overlaps all or a portion of the amino acid sequence set forth in NKYAASSYLSL (SEQ ID NO: 2). In some aspects, the anti-FLC antibody binds an epitope on lambda light chain comprising the amino acid sequence set forth in NKYAASSYLSL (SEQ ID NO: 2).

I. Terms

In order that the present disclosure can be more readily understood, certain terms are first defined. As used in this application, except as otherwise expressly provided herein, each of the following terms shall have the meaning set forth below. Additional definitions are set forth throughout the application.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As described herein heterologous with respect to an amino acid or nucleic acid sequence refers to a sequence of a different source or origin compared to amino acid or nucleic acid sequence to which the heterologous sequence is compared.

An "antibody" (Ab), as used herein, includes, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term "antibody" includes monoclonal antibodies, and includes intact antibodies and functional (antigen-binding) antibody fragments thereof, including fragment antigen binding (Fab) fragments, F(ab')₂ fragments, Fab' fragments, Fv fragments, recombinant IgG (rIgG) fragments, single chain antibody fragments, including single chain variable fragments (sFv or scFv), and single domain antibodies (e.g., sdAb, sdFv, nanobody) fragments.

The terms "complementarity determining region," and "CDR," which are synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4). The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273, 927-948 ("Chothia" numbering scheme); MacCallum et al., *J. Mol. Biol.* 262:732-745 (1996), "Antibody-antigen interactions: Contact analysis and binding site topography," *J Mol. Biol.* 262, 732-745." ("Contact" numbering scheme); Lefranc M P et al., "IMGT unique numbering for immunoglobulin and T cell receptor variable domains and Ig superfamily V-like domains," Dev Comp *Immunol,* 2003 January; 27(1):55-77 ("IMGT" numbering scheme); Honegger A and Pluckthun A, "Yet another numbering scheme for immunoglobulin variable domains: an automatic modeling and analysis tool," *J Mol Biol,* 2001 Jun. 8; 309(3):657-70, ("Aho" numbering scheme); and Whitelegg N R and Rees A R, "WAM: an improved algorithm for modelling antibodies on the WEB," *Protein Eng.* 2000 December; 13(12):819-24 ("AbM" numbering scheme. In certain embodiments, the CDRs of the antibodies described herein can be defined by a method selected from Kabat, Chothia, IMGT, Aho, AbM, or combinations thereof.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs (See e.g., Kindt et al. Kuby *Immunology,* 6th ed., W. H. Freeman and Co., page 91(2007)). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively (See e.g., Portolano et al., *J. Immunol.* 150:880-887 (1993); Clarkson et al., *Nature* 352:624-628 (1991)).

As used herein, an "intermediate" light chain refers to a light chain immunoglobulin polypeptide that is not a mature light chain immunoglobulin. In some aspects, the intermediate light chain is an unfolded light chain polypeptide. In some aspects, the intermediate light chain is a misfolded light chain polypeptide.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class or subclass (e.g., IgM or IgG1) that is encoded by the heavy chain constant region genes. The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

An "isolated antibody" refers to an antibody that is substantially free of other antibodies having different antigenic specificities. An isolated antibody that binds specifically to an antigen can, however, have cross-reactivity to other antigens, such as antigens from different species. Moreover, an isolated antibody can be substantially free of other cellular material and/or chemicals.

The term "monoclonal antibody" ("mAb") refers to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody MAbs can be produced by hybridoma, recombinant, transgenic or other techniques known to those skilled in the art.

The term "polyclonal antibody" ("pAb") refers to a non-naturally occurring preparation of antibody molecules of more than one molecular composition, i.e., antibody molecules whose primary sequences are not necessarily the same, and which can exhibit variable binding specificity and affinity for a particular epitope.

A "human" antibody refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers to an antibody in which some, most, or all of the amino acids outside the CDR domains of a non-human antibody are replaced with corresponding amino acids derived from human immunoglobulins. In one aspect of a humanized form of an antibody, some, most, or all of the amino acids outside the CDR domains have been replaced with amino acids from human immunoglobulins, whereas some, most, or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody A "chimeric antibody" refers to an antibody in which the variable regions are derived from one species and the constant regions are derived from another species, such as an antibody in which the variable regions are derived from a mouse antibody and the constant regions are derived from a human antibody An "antigen" refers to any molecule, e.g., a peptide, that is capable of being bound by an antibody or that provokes an immune response. An "epitope," as used herein, refers to a portion of a polypeptide that is capable of being bound by an antibody or that provokes an immune response. A person of skill in the art would readily understand that any macromolecule, including virtually all proteins or peptides, can serve as an antigen. An antigen and/or an epitope can be endogenously expressed, i.e. expressed by genomic DNA, or can be recombinantly expressed from an exogenous DNA. An antigen and/or an epitope can be specific to a certain tissue, such as a cancer cell, or it can be broadly expressed. In addition, fragments of larger molecules can act as antigens. In one aspect, antigens are tumor antigens. An epitope can be present in a longer polypeptide (e.g., in a protein), or an epitope can be present as a fragment of a longer polypeptide. In some aspects, an epitope is complexed with a major histocompatibility complex (MHC; also referred to herein as complexed with an HLA molecule, e.g., an HLA class 1 molecule). In certain embodiments, epitopes include certain non-proteins molecules (e.g., sugars, lipids, phosphates etc.) or non-protein molecules that modify amino acids of protein molecules.

An "anti-antigen" antibody refers to an antibody that binds specifically to the antigen. For example, an anti-FLC antibody binds specifically to FLC.

An "antigen-binding portion" of an antibody (also called an "antigen-binding fragment") refers to one or more fragments of an antibody that retain the ability to bind specifically to the antigen bound by the whole antibody.

Percent (%) sequence identity with respect to a reference polypeptide sequence is the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways using available computer software. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Amyloidosis," as used herein, refers to a disease or condition characterized by the misfolding of free immunoglobulin light chains (LC) which can deposit as light chain amyloid (AL) in the heart, kidneys, or liver. The condition is caused by an underlying plasma cell dyscrasia that results in plasma cells secreting a large excess of free immunoglobulin kappa (κ) and/or lambda (λ) light chains into circulation. "Primary amyloidosis" or "AL amyloidosis," as used herein, refers to the most common type of systemic amyloidosis, with an incidence of 9-14 people per million per year in the Western world.

"Plasma cell dyscrasia," as used herein, refers to a proliferative plasma cell disorder under which a single, aberrant plasma cell clone (a terminally differentiated B cell) undergoes unregulated expansion and produces above-normal amounts of light chain protein. Plasma cell dyscrasias are classified as either benign, as seen in monoclonal gammopathies of unknown significance (MGUS), or malignant, as in multiple myeloma (MM) and plasma cell leukemia (PCL). Regardless of the type of dyscrasia involved, these secreted light chains can undergo misfolding events that render them prone to aggregate and accumulate as amyloid in vital organs including the heart, kidneys and nervous system. Such infiltration can result in nephrotic syndrome, hepatomegaly, peripheral neuropathy, restrictive cardiomyopathy, and ultimately death.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some aspects, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

"Treat," "treatment," or "treating," as used herein refers to, e.g., a deliberate intervention to a physiological disease state resulting in the reduction in severity of a disease or condition; the reduction in the duration of a condition course; the amelioration or elimination of one or more symptoms associated with a disease or condition; or the provision of beneficial effects to a subject with a disease or condition. Treatment does not require curing the underlying disease or condition.

A "therapeutically effective amount," "effective dose," "effective amount," or "therapeutically effective dosage" of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, administering an antibody or an antigen-binding portion thereof that stimulates an immune response in the subject.

Various aspects of the disclosure are described in further detail in the following subsections.

II. Compositions of the Disclosure

Certain aspects of the present disclosure are directed to antibodies that specifically bind human free immunoglobulin light chain (FLC; "anti-FLC antibody"). Immunoglobulins by their nature have highly variable amino acid sequences. Further, AL deposits typical of amyloidosis comprise aggregates of misfolded free immunoglobulin light chains (LC). As a result, targeting of FLC requires the ability to recognize a constant among many variable sequences. To overcome this heterogeneity, the antibodies described herein are specifically designed to recognize an epitope in the constant region of the immunoglobulin light chain sequence.

In certain aspects, the anti-FLC antibodies bind immunoglobulin light chain polypeptides regardless of the antigen specificity of the immunoglobulin light chains. In some aspects, the anti-FLC antibodies bind an epitope on an immunoglobulin light chain polypeptide, wherein the epitope is located within the constant region of the immunoglobulin light chain. In some aspects, the epitope is located within a portion of the immunoglobulin light chain constant region that is conformationally inaccessible when the immunoglobulin light chain is in a complex with an immunoglobulin heavy chain. In some aspects, the epitope is located within a portion of the immunoglobulin light chain constant region that is not surface exposed when the immunoglobulin light chain is in a complex with an immunoglobulin heavy chain. In some aspects, the anti-FLC antibody specifically binds to an epitope located within the constant region of the immunoglobulin light chain, wherein the anti-FLC antibody only binds the epitope when the immunoglobulin light chain is not in a complex with an immunoglobulin heavy chain.

In certain aspects, the anti-FLC antibody binds specifically to an immunoglobulin light chain that is not associated with an immunoglobulin heavy chain. In some aspects, the anti-FLC antibody does not bind a complex comprising immunoglobulin light chain covalently linked to immunoglobulin heavy chain.

The anti-FLC antibodies disclosed herein are capable of binding free immunoglobulin light chains of any make up and of any origin. In some aspects, the anti-FLC antibodies disclosed herein bind any immunoglobulin light chain comprising all or a portion of the light chain constant region. In some aspects, the FLC comprises a full length immunoglobulin light chain peptide. In some aspects, the FLC comprises a fragment of an immunoglobulin light chain peptide. In some aspects, the fragment of the immunoglobulin light chain peptide comprises all or a portion of the light chain constant region. In some aspects, the FLC comprises an aggregate of immunoglobulin light chain peptides. In some aspects, the aggregate comprises full length immunoglobulin light chain peptides. In some aspects, the aggregate comprises fragments of immunoglobulin light chain peptides. In some aspects, the aggregate comprises both full length immunoglobulin light chain peptides and fragments of immunoglobulin light chain peptides. In some aspects, the aggregate of immunoglobulin light chain peptides comprises one or more misfolded immunoglobulin light chain peptides.

In some aspects, the anti-FLC antibody binds one or more light chain amyloid fibrils. In some aspects, the anti-FLC antibody is capable of binding light chain amyloid fibrils in vivo. In some aspects, the anti-FLC antibody selectively binds light chain fibrils more efficiently than it binds natively folded light chain. In some aspects, the anti-FLC antibody selectively binds light chain fibrils at least 1.5 times, at least 2.0 times, at least 2.5 times, at least 3.0 times, at least 3.5 times, at least 4.0 times, at least 4.5 times, at least 5 times, at least 6 times, at least 7 times, at least 8 times, at least 9 times, or at least 10 times more efficiently than it binds natively folded light chain. In some aspects, the anti-FLC antibody selectively binds light chain fibrils more efficiently than it binds natively folded light chain. In some aspects, the anti-FLC antibody selectively binds light chain fibrils at least 2.0 times more efficiently than it binds natively folded light chain. In some aspects, the amyloid fibrils are collected from a biological sample obtained from a subject. In some aspects, the biological sample is selected from blood, serum, plasma, solid tissue, and any combination thereof.

In some aspects, the anti-FLC antibody is capable of disrupting light chain fibril formation. In some aspects, the anti-FLC antibody disrupts light chain fibril formation by misfolded light chain intermediates in solution. In some aspects, the anti-FLC antibody disrupts light chain fibril formation from misfolded light chain intermediates in vivo.

In some aspects, the anti-FLC antibody is capable of reducing light chain fibril formation. In some aspects, the anti-FLC antibody reduces light chain fibril formation by misfolded light chain intermediates in solution. In some aspects, the anti-FLC antibody reduces light chain fibril formation by misfolded light chain intermediates in vivo. In some aspects, the anti-FLC antibody reduces light chain fibril formation by at least about 1.5 fold, at least about 2.0 fold, at least about 2.5 fold, at least about 3.0 fold, at least about 3.5 fold, at least about 4.0 fold, at least about 4.5 fold, at least about 5 fold, at least about 6 fold, at least about 7 fold, at least about 8 fold, at least about 9 fold, or at least about 10 fold, relative to the formation of light chain fibrils under similar conditions lacking the anti-FLC antibody.

In some aspects, the anti-FLC antibody is capable of inducing an immune response in vivo. In some aspects, binding of the anti-FLC antibody to an immunoglobulin light chain, e.g., in an amyloid fibril, in a subject induces and/or enhances an immune response in the subject. In some aspects, the immune response is a cellular immune response. In some aspects, the immune response comprises clearing, removing, and/or dissociating an immunoglobulin light chain aggregate, e.g., an amyloid fibril, in the subject. In some aspects, the anti-FLC antibody enhances an immune response by at least about 1.5 fold, at least about 2.0 fold, at least about 2.5 fold, at least about 3.0 fold, at least about 3.5 fold, at least about 4.0 fold, at least about 4.5 fold, at least about 5 fold, at least about 6 fold, at least about 7 fold, at least about 8 fold, at least about 9 fold, or at least about 10 fold, relative to an immune response in a subject not administered the anti-FLC antibody. In some aspects, the anti-FLC antibody induces an immune response in a subject against an immunoglobulin light chain aggregate, e.g., an amyloid fibril, wherein the subject would not have had an immune response against the immunoglobulin light chain aggregate, e.g., an amyloid fibril, in the absence of the anti-FLC antibody.

In some aspects, the anti-FLC antibody is capable of opsinizing a light chain immunoglobulin aggregate, e.g., an amyloid fibril, in a subject. In some aspects, the anti-FLC antibody is capable of inducing removal of a light chain immunoglobulin aggregate, e.g., an amyloid fibril, in a subject.

In some aspects, the anti-FLC antibody is a polyclonal antibody. In some aspects, the anti-FLC antibody is a monoclonal antibody. In some aspects, the anti-FLC antibody is a chimeric antibody. In some aspects, the anti-FLC antibody is a humanized antibody. In some aspects, the anti-FLC antibody is a human antibody.

In some aspects, the anti-FLC antibody comprises an antigen-binding portion of an antibody. In some aspects, the anti-FLC antibody comprises a Fab. In some aspects, the anti-FLC antibody comprises a Fab'. In some aspects, the anti-FLC antibody comprises a F(ab')2. In some aspects, the anti-FLC antibody comprises a scFv. In some aspects, the anti-FLC antibody comprises a dsFv. In some aspects, the anti-FLC antibody comprises a ds-scFv. In some aspects, the anti-FLC antibody comprises a dimer. In some aspects, the anti-FLC antibody comprises a minibody. In some aspects, the anti-FLC antibody comprises a diabody. In some aspects, the anti-FLC antibody comprises a multimer of any of the above. In some aspects, the anti-FLC antibody comprises a bispecific antibody fragment. In some aspects, the anti-FLC antibody is a single chain antibody.

Immunoglobulin light chains are expressed from two loci in the human genome: the immunoglobulin kappa locus, which encodes the kappa light chain; and the immunoglobulin lambda locus, which encodes the lambda light chain. Each B lymphocyte expresses only one class of light chain, either from the kappa or the lambda locus. As a result, human serum comprises a mix of kappa light chain and lambda light chain antibodies. The canonical amino acid sequences for kappa light chain (UniProt P0DOX7; SEQ ID NO: 5) and lambda light chain (UniProt P0DOX8; SEQ ID NO: 7) are shown in Table 1.

TABLE 1

Human Immunoglobulin Light Chain Sequences

| SEQ ID NO | Description | Sequence |
|---|---|---|
| 5 | hIg LC Kappa | DIQMTQSPSTLSASVGDRVTITCRASQSINTWLAWYQQKPGKAPKLLMYKASSL ESGVPSRFIGSGSGTEFTLTISSLQPDDFATYYCQQYNSDSKMFGQGTKVEVKG TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSENRGEC |
| 6 | hIG LC Kappa Constant | TVAAPSVFIFPPSDEQLKSGTASVVCLLNNFYPREAKVQWKVDNALQSGNSQES VTEQDSKDSTYSLSSTLTLSKADYEKHKVYACEVTHQGLSSPVTKSENRGEC |
| 7 | hIg LC Lambda | QSALTQPPSASGSLGQSVTISCTGTSSDVGGYNYVSWYQQHAGKAPKVIIYEVN KRPSGVPDRESGSKSGNTASLTVSGLQAEDEADYYCSSYEGSDNFVFGTGTKVT VLGQPKANPTVTLFPPSSEELQANKATLVCLISDFYPGAVTVAWKADGSPVKAG VETTKPSKQSNNKYAASSYLSLTPEQWKSHRSYSCQVTHEGSTVEKTVAPTECS |
| 8 | hIG LC Lambda Constant | QPKANPTVTLFPPSSEELQANKATLVCLISDFYPGAVTVAWKADGSPVKAGVET TKPSKQSNNKYAASSYLSLTPEQWKSHRSYSCQVTHEGSTVEKTVAPTECS |

As noted above, each immunoglobulin light chain comprises a variable domain and a constant domain. The kappa light chain variable domain extends from amino acid residues 1 to 108 of SEQ ID NO: 5, and the kappa light chain constant region extends from amino acid residues 109-214 of SEQ ID NO: 5 (captured as SEQ ID NO: 6). The lambda light chain variable domain extends from amino acid residues 1 to 112 of SEQ ID NO: 7, and the lambda light chain constant region extends from amino acid residues 112-216 of SEQ ID NO: 7 (captured as SEQ ID NO: 8).

II.A. Anti-Kappa Light Chain Antibodies

In some aspects, the anti-FLC antibody specifically binds a kappa light chain polypeptide. In some aspects, the anti-FLC antibody specifically binds misfolded kappa light chain polypeptide. In some aspects, the anti-FLC antibody binds misfolded kappa light chain polypeptide and does not bind native kappa light chain polypeptide. In some aspects, the anti-FLC antibody specifically binds unfolded kappa light chain polypeptide. In some aspects, the anti-FLC antibody binds unfolded kappa light chain polypeptide and does not bind natively folded kappa light chain polypeptide.

In some aspects, the anti-FLC antibody binds an epitope present in the constant region of the kappa light chain. In some aspects, the epitope is surface displayed in misfolded kappa light chain polypeptide. In some aspects, the epitope is surface displayed in unfolded kappa light chain polypeptide. In some aspects, the epitope is not surface displayed in natively folded kappa light chain polypeptide.

In some aspects, the anti-FLC antibody cross-competes for binding a kappa light chain polypeptide with a reference antibody, wherein the reference antibody binds one or more amino acid of an epitope comprising the amino acid sequence set forth in STYSLSSTLT (SEQ ID NO: 1). In some aspects, the anti-FLC antibody binds kappa light chain at an epitope that overlaps all or a portion of the amino acid sequence set forth in STYSLSSTLT (SEQ ID NO: 1). In some aspects, the anti-FLC antibody binds an epitope on kappa light chain comprising the amino acid sequence set forth in STYSLSSTLT (SEQ ID NO: 1). In certain embodiments, the reference antibody comprises a heavy chain variable region amino acid sequence and a light chain variable region amino acid sequence of SEQ ID NO: 14 and SEQ ID NO: 10, respectively.

In some aspects, the epitope comprises at least one, at least two, at least three, at least four at least five, at least six, at least seven, at least eight, at least nine, or ten of the amino acids set forth in SEQ ID NO: 1. In some aspects, the epitope comprises $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, $Thr_{180}$, or any combination thereof, corresponding to SEQ ID NO: 5. In some aspects, the epitope comprises $Ser_{171}$, corresponding to SEQ ID NO: 5. In some aspects, the epitope comprises $Thr_{172}$, corresponding to SEQ ID NO: 5. In some aspects, the epitope comprises $Tyr_{173}$, corresponding to SEQ ID NO: 5. In some aspects, the epitope comprises $Ser_{174}$, corresponding to SEQ ID NO: 5. In some aspects, the epitope comprises $Leu_{175}$, $Ser_{176}$, corresponding to SEQ ID NO: 5. In some aspects, the epitope comprises $Ser_{177}$, corresponding to SEQ ID NO: 5. In some aspects, the epitope comprises $Thr_{178}$, corresponding to SEQ ID NO: 5. In some aspects, the epitope comprises $Leu_{179}$, corresponding to SEQ ID NO: 5. In some aspects, the epitope comprises $Thr_{180}$, corresponding to SEQ ID NO: 5.

In some aspects, the epitope comprises at least two of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least three of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least four of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least five of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least six of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least seven of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least eight of $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises at least nine of $Ser_{171}$, $Thr_{172}$, $Tyr_{173}$, $Ser_{174}$, $Leu_{175}$, $Ser_{176}$, $Ser_{178}$, $Thr_{179}$, $Leu_{179}$, and $Thr_{180}$, corresponding to SEQ ID NO: 5. In some aspects, the epitope comprises $Ser_{171}$, $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5.

In some aspects, the epitope comprises $Ser_{171}$ and $Thr_{172}$, corresponding to SEQ ID NO: 5. In some aspects, the epitope comprises $Ser_{171}$, $Thr_{172}$, and $Tyr_{173}$, corresponding to SEQ ID NO: 5. In some aspects, the epitope comprises $Ser_{171}$, $Thr_{172}$, $Tyr_{173}$, and $Ser_{174}$, corresponding to SEQ ID NO: 5. In some aspects, the epitope comprises $Ser_{171}$, $Thr_{172}$, $Tyr_{173}$, $Ser_{174}$, and $Leu_{175}$, corresponding to SEQ ID NO: 5. In some aspects, the epitope comprises $Ser_{171}$, $Thr_{172}$, $Tyr_{173}$, $Ser_{174}$, $Leu_{175}$, and $Ser_{176}$, corresponding to SEQ ID NO: 5. In some aspects, the epitope comprises $Ser_{171}$, $Thr_{172}$, $Tyr_{173}$, $Ser_{174}$, $Leu_{175}$, $Ser_{176}$, and $Ser_{177}$, corresponding to SEQ ID NO: 5. In some aspects, the epitope comprises $Ser_{171}$, $Thr_{172}$, $Tyr_{173}$, $Ser_{174}$, $Leu_{175}$, $Ser_{176}$, $Ser_{177}$, and $Thr_{178}$, corresponding to SEQ ID NO: 5. In some aspects, the epitope comprises $Ser_{171}$, $Thr_{172}$, $Tyr_{173}$, $Ser_{174}$, $Leu_{175}$, $Ser_{176}$, $Ser_{177}$, $Thr_{178}$, and $Leu_{179}$, corresponding to SEQ ID NO: 5.

In some aspects, the epitope comprises $Leu_{179}$ and $Thr_{180}$, corresponding to SEQ ID NO: 5. In some aspects, the epitope comprises $Thr_{178}$, $Leu_{179}$, and $Thr_{180}$, corresponding to SEQ ID NO: 5. In some aspects, the epitope comprises $Ser_{177}$, $Thr_{178}$, $Leu_{179}$, and $Thr_{180}$, corresponding to SEQ ID NO: 5. In some aspects, the epitope comprises $Ser_{176}$, $Ser_{177}$, $Thr_{178}$, $Leu_{179}$, and $Thr_{180}$, corresponding to SEQ ID NO: 5. In some aspects, the epitope comprises $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5. In some aspects, the epitope comprises $Thr_{172}$, $Tyr_{173}$, $Ser_{174}$, $Leu_{175}$, $Ser_{176}$, $Ser_{177}$, $Thr_{178}$, $Leu_{179}$, and $Thr_{180}$, corresponding to SEQ ID NO: 5.

In some aspects, the anti-FLC antibody specifically binds a kappa light chain polypeptide and comprises (i) a heavy chain and (ii) a light chain; wherein the heavy chain comprises a variable region and a constant region; wherein the heavy chain variable region comprises a variable heavy chain complementarity determining region (VH-CDR) 1, VH-CDR2, and VH-CDR3; and wherein the light chain variable region comprises a variable light chain (VL) CDR1, VL-CDR2, and a VL-CDR3. In some aspects, the VL-CDR1 comprises the amino acid sequence set forth in SEQ ID NO: 11. In some aspects, the VL-CDR2 comprises the amino acid sequence set forth in SEQ ID NO: 12. In some aspects, the VL-CDR3 comprises the amino acid sequence set forth in SEQ ID NO: 13. In some aspects, the VH-CDR1 comprises the amino acid sequence set forth in SEQ ID NO: 15. In some aspects, the VH-CDR2 comprises the amino acid sequence set forth in SEQ ID NO: 16. In some aspects, the VH-CDR3 comprises the amino acid sequence set forth in SEQ ID NO: 17.

TABLE 2

Anti-Kappa Light Chain Monoclonal Antibody Sequences (LX-96)

| | |
|---|---|
| Heavy Chain Variable | QVQLQQPGAELARPGASVKLSCKASGYTFTSFWIQWIKQRPGQGLEWIGSIYPGDGDTRYIQKF RGKATLTADESSSTAYMQLSSLASEDSAIYYCAIVTTAPDYWGQGTTLTVSS (SEQ ID NO: 14) |
| VH-CDR1 | SEWIQ (SEQ ID NO: 15) |
| VH-CDR2 | SIYPGDGDTRYIQKFRG (SEQ ID NO: 16) |
| VH-CDR3 | VTTAPDY (SEQ ID NO: 17) |
| Light Chain Variable | DVVMTQTPLTLSVTVGQPASISCKSSQSLLDGDGKTYLNWLLQRPGQSPKRLIY LVSKLDSGVPDRFTGSGSGTDFTLKISRVEAEDLGIYYCWQGTHFPQTFGGGTK LEIK (SEQ ID NO: 10) |
| VL-CDR1 | KSSQSLLDGDGKTYLN (SEQ ID NO: 11) |
| VL-CDR2 | LVSKLDS (SEQ ID NO: 12) |
| VL-CDR3 | WQGTHEPQT (SEQ ID NO: 13) |

In some aspects, the anti-FLC antibody comprises a (i) a heavy chain and (ii) a light chain; wherein the heavy chain comprises a variable region and a constant region; wherein the heavy chain variable region comprises a VH-CDR1, VH-CDR2, and VH-CDR3; and wherein the light chain variable region comprises a variable light chain (VL) CDR1, VL-CDR2, and a VL-CDR3; wherein the VH-CDR1 comprises the amino acid sequence set forth in SEQ ID NO: 15; the VH-CDR2 comprises the amino acid sequence set forth in SEQ ID NO: 16; and the VH-CDR3 comprises the amino acid sequence set forth in SEQ ID NO: 17. In some aspects, the VL-CDR1 comprises the amino acid sequence set forth in SEQ ID NO: 11, the VL-CDR2 comprises the amino acid sequence set forth in SEQ ID NO: 12, and the VL-CDR3 comprises the amino acid sequence set forth in SEQ ID NO: 13.

In some aspects, the anti-FLC antibody comprises a (i) a heavy chain and (ii) a light chain; wherein the heavy chain comprises a variable region and a constant region; wherein the heavy chain variable region comprises a VH-CDR1, VH-CDR2, and VH-CDR3; and wherein the light chain variable region comprises a variable light chain (VL) CDR1, VL-CDR2, and a VL-CDR3; wherein the VL-CDR1 comprises the amino acid sequence set forth in SEQ ID NO: 11, the VL-CDR2 comprises the amino acid sequence set forth in SEQ ID NO: 12, and the VL-CDR3 comprises the amino acid sequence set forth in SEQ ID NO: 13. In some aspects, the VH-CDR1 comprises the amino acid sequence set forth in SEQ ID NO: 15; the VH-CDR2 comprises the amino acid sequence set forth in SEQ ID NO: 16; and the VH-CDR3 comprises the amino acid sequence set forth in SEQ ID NO: 17.

In certain aspects, the anti-FLC antibody comprises a (i) a heavy chain and (ii) a light chain; wherein the heavy chain comprises a variable region and a constant region; wherein the heavy chain variable region comprises a VH-CDR1, VH-CDR2, and VH-CDR3; and wherein the light chain variable region comprises a variable light chain (VL) CDR1, VL-CDR2, and a VL-CDR3; wherein the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 15; the VH-CDR2 comprises the amino acid sequence set forth in SEQ ID NO: 16; and the VH-CDR3 comprises the amino acid sequence set forth in SEQ ID NO: 17.

In some aspects, the anti-FLC antibody comprises a heavy chain variable region comprising an amino acid sequence having at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 90% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 95% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 96% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 97% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 98% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising an amino acid sequence having at least about 99% sequence identity to the amino acid sequence set forth in SEQ ID NO: 14; wherein the heavy chain variable region comprises a VH-CDR1 comprising the amino acid sequence set forth in SEQ ID NO: 15, a VH-CDR2 comprising the amino acid sequence set forth in SEQ ID NO: 16, and a VH-CDR3 comprising the amino acid sequence set forth in SEQ ID NO: 17. In some aspects, the anti-FLC antibody comprises a heavy chain variable region comprising the amino acid sequence set forth in SEQ ID NO: 14.

In some aspects, the anti-FLC antibody comprises a light chain variable region comprising an amino acid sequence having at least about 75%, at least about 80%, at least about 85%, at least about 90%, at least about 95%, at least about 96%, at least about 97%, at least about 98%, or at least about 99% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 90% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 95% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 96% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 97% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 98% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising an amino acid sequence having at least about 99% sequence identity to the amino acid sequence set forth in SEQ ID NO: 10; wherein the light chain variable region comprises a VL-CDR1 comprising the amino acid sequence set forth in SEQ ID NO: 11, a VL-CDR2 comprising the amino acid sequence set forth in SEQ ID NO: 12, and a VL-CDR3 comprising the amino acid sequence set forth in SEQ ID NO: 13. In some aspects, the anti-FLC antibody comprises a light chain variable region comprising the amino acid sequence set forth in SEQ ID NO: 10.

In some aspects, the anti-FLC antibody comprises a heavy chain variable region comprising the amino acid sequence set forth in SEQ ID NO: 14 and a light chain variable region comprising the amino acid sequence set forth in SEQ ID NO: 10.

In some aspects, the anti-FLC antibody comprises a heavy chain comprising the amino acid sequence set forth in SEQ ID NO: 18 and a light chain comprising the amino acid sequence set forth in SEQ ID NO: 19. In certain embodiments, the antibody lacks the secretory leader sequence of the heavy and light chain.

In some aspects, the anti-FLC antibody compete for binding to a kappa light chain polypeptide with a reference antibody, wherein the reference antibody comprises a (i) a heavy chain and (ii) a light chain; wherein the heavy chain comprises a variable region and a constant region; wherein the heavy chain variable region comprises a VH-CDR1, VH-CDR2, and VH-CDR3; and wherein the light chain variable region comprises a variable light chain (VL) CDR1, VL-CDR2, and a VL-CDR3; wherein the VL-CDR1 comprises the amino acid sequence set forth in SEQ ID NO: 11, the VL-CDR2 comprises the amino acid sequence set forth in SEQ ID NO: 12, the VL-CDR3 comprises the amino acid sequence set forth in SEQ ID NO: 13, the VH-CDR1 comprises the amino acid sequence set forth in SEQ ID NO: 14; the VH-CDR2 comprises the amino acid sequence set forth in SEQ ID NO: 15; and the VH-CDR3 comprises the amino acid sequence set forth in SEQ ID NO: 16. In some aspects, the reference antibody comprises a heavy chain variable region comprising the amino acid sequence set forth in SEQ ID NO: 14 and a light chain variable region comprising the amino acid sequence set forth in SEQ ID NO: 10.

In some embodiments, the anti-kappa light chain antibodies provided herein bind to misfolded kappa light chains with a dissociation constant ($K_D$) of about 1 $\mu$M, 100 nM, 50 nM, 40 nM, 30 nM, 20 nM, 15 nM, 10 nM, 5 nM, 2 nM, 1 nM, 0.5 nM, 0.1 nM, 0.05 nM, 0.01 nM or less (e.g., $10^{-8}$ M or less, e.g., from $10^{-8}$ M to $10^{-13}$ M, e.g., from $10^{-9}$ M to $10^{-13}$ M) for the antibody target. In some embodiments, an antibody provided herein has a dissociation constant ($K_D$) of about 100 nM, 50 nM, 40 nM, 30 nM, 20 nM, 15 nM, 10 nM, 5 nM, 2 nM, 1 nM, 0.5 nM, 0.1 nM, 0.05 nM, 0.01 nM, or 0.001 nM or greater (e.g., $10^{-8}$ M or less, e.g., from $10^{-8}$ M to $10^{-13}$ M, e.g., from $10^{-9}$ M to $10^{-13}$ M) for the antibody target. The antibody may bind with a KD of between 100 pM and 100 nM, 100 pM and 50 nM, 100 pM and 10 nM, 500 pM and 100 nM, 500 pM and 50 nM, 500 pM and 10 nM, 1 nM and 100 nM, 1 nM and 50 nM, 1 nM and 10 nM $K_D$ can be measured by a suitable assay including bio-layer interferometry as described herein.

In certain embodiments, the anti-kappa light chain antibody binds to AL09 amyloid with a $K_D$ of between 500 picomolar and 25 nanomolar. In certain embodiments, the anti-kappa light chain antibody binds to AL09 amyloid with a $K_D$ of between 500 picomolar and 10 nanomolar. In certain embodiments, the anti-kappa light chain antibody binds to AL09 amyloid with a $K_D$ of between 1 picomolar and 10 nanomolar.

II.B. Anti-Lambda Light Chain Antibodies

In some aspects, the anti-FLC antibody binds a lambda light chain. In some aspects, the anti-FLC antibody cross competes with a reference antibody for binding to lambda light chain, wherein the reference antibody binds an epitope on immunoglobulin lambda light chain comprising the amino acid sequence set forth in In some aspects, the anti-FLC antibody binds lambda light chain at an epitope that overlaps all or a portion of the amino acid sequence set forth in NKYAASSYLSL (SEQ ID NO: 2). In some aspects, the anti-FLC antibody binds an epitope on lambda light chain comprising the amino acid sequence set forth in NKYAASSYLSL (SEQ ID NO: 2).

In some aspects, the anti-FLC antibody specifically binds a lambda light chain polypeptide. In some aspects, the anti-FLC antibody binds an epitope present in the constant region of the lambda light chain.

In some aspects, the anti-FLC antibody cross-competes for binding a lambda light chain polypeptide with a reference antibody, wherein the reference antibody binds one or more amino acid of an epitope comprising the amino acid sequence set forth in NKYAASSYLSL (SEQ ID NO: 2). In some aspects, the anti-FLC antibody binds lambda light chain at an epitope that overlaps all or a portion of the amino acid sequence set forth in NKYAASSYLSL (SEQ ID NO: 2). In some aspects, the anti-FLC antibody binds an epitope on lambda light chain comprising the amino acid sequence set forth in NKYAASSYLSL (SEQ ID NO: 2).

In some aspects, the epitope comprises at least one, at least two, at least three, at least four at least five, at least six, at least seven, at least eight, at least nine, or ten of the amino acids set forth in SEQ ID NO: 2. In some aspects, the epitope comprises $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, $Leu_{184}$, or any combination thereof, corresponding to SEQ ID NO: 7. In some aspects, the epitope comprises $Asn_{174}$, corresponding to SEQ ID NO: 7. In some aspects, the epitope comprises $Lys_{175}$, corresponding to SEQ ID NO: 7. In some aspects, the epitope comprises $Tyr_{176}$, corresponding to SEQ ID NO: 7. In some aspects, the epitope comprises $Ala_{177}$, corresponding to SEQ ID NO: 7. In some aspects, the epitope comprises $Ala_{178}$, corresponding to SEQ ID NO: 7. In some aspects, the epitope comprises $Ser_{179}$, corresponding to SEQ ID NO: 7. In some aspects, the epitope comprises $Ser_{180}$, corresponding to SEQ ID NO: 7. In some aspects, the epitope comprises $Tyr_{181}$, corresponding to SEQ ID NO: 7. In some aspects, the epitope comprises $Leu_{182}$, corresponding to SEQ ID NO: 7. In some aspects, the epitope comprises $Ser_{183}$, corresponding to SEQ ID NO: 7. In some aspects, the epitope comprises $Leu_{184}$, corresponding to SEQ ID NO: 7.

In some aspects, the epitope comprises at least two of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least three of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least four of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least five of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least six of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least seven of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least eight of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises at least nine of $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7.

In some aspects, the epitope comprises $Asn_{174}$ and $Lys_{175}$, corresponding to SEQ ID NO: 7. In some aspects, the epitope comprises $Asn_{174}$, $Lys_{175}$, and $Tyr_{176}$, corresponding to SEQ ID NO: 7. In some aspects, the epitope comprises $Asn_{174}$, $Lys_{175}$, $Tyr_{176}$, and $Ala_{177}$, corresponding to SEQ ID NO: 7. In some aspects, the epitope comprises $Asn_{174}$, $Lys_{175}$, $Tyr_{176}$, $Ala_{177}$, and $Ala_{178}$, corresponding to SEQ ID NO: 7. In some aspects, the epitope comprises $Asn_{174}$, $Lys_{175}$, $Tyr_{176}$, $Ala_{177}$, $Ala_{178}$, and $Ser_{179}$, corresponding to SEQ ID NO: 7. In some aspects, the epitope comprises $Asn_{174}$, $Lys_{175}$, $Tyr_{176}$, $Ala_{177}$, $Ala_{178}$, $Ser_{179}$, and $Ser_{180}$, corresponding to SEQ ID NO: 7. In some aspects, the epitope comprises $Asn_{174}$, $Lys_{175}$, $Tyr_{176}$, $Ala_{177}$, $Ser_{179}$, $Ser_{180}$, and $Tyr_{181}$, corresponding to SEQ ID NO: 7. In some aspects, the epitope comprises $Asn_{174}$, $Lys_{175}$, $Tyr_{176}$, $Ala_{177}$, $Ala_{178}$, $Ser_{179}$, $Ser_{180}$, $Tyr_{181}$, and $Leu_{182}$. In some aspects, the epitope comprises $Asn_{174}$, $Lys_{175}$, $Tyr_{176}$, $Ala_{177}$, $Ala_{178}$, $Ser_{179}$, $Ser_{180}$, $Tyr_{181}$, $Leu_{182}$, and $Ser_{183}$, corresponding to SEQ ID NO: 7.

In some aspects, the epitope comprises $Ser_{183}$ and $Leu_{184}$, corresponding to SEQ ID NO: 7. In some aspects, the epitope comprises $Leu_{182}$, $Ser_{183}$, and $Leu_{184}$, corresponding to SEQ ID NO: 7. In some aspects, the epitope comprises $Tyr_{181}$, $Leu_{182}$, $Ser_{183}$, and $Leu_{184}$, corresponding to SEQ ID NO: 7. In some aspects, the epitope comprises $Ser_{180}$, $Tyr_{181}$, $Leu_{182}$, $Ser_{183}$, and $Leu_{184}$, corresponding to SEQ ID NO: 7. In some aspects, the epitope comprises $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7. In some aspects, the epitope comprises $Lys_{175}$, $Tyr_{176}$, $Ala_{177}$, $Ala_{178}$, $Ser_{179}$, $Ser_{180}$, $Tyr_{181}$, $Leu_{182}$, $Ser_{183}$, and $Leu_{184}$, corresponding to SEQ ID NO: 7.

II.C. Nucleic Acid Molecules

Certain aspects of the present disclosure are directed to nucleic acid molecules that encode the anti-FLC antibodies described herein. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis and others well known in the art. See, F. Ausubel, et al., ed. (1987) Current Protocols in Molecular Biology, Greene Publishing and Wiley Interscience, New York. A nucleic acid described herein can be, for example, DNA or RNA and can or cannot contain intronic sequences. In some aspects, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

A method for making the anti-FLC antibodies disclosed herein can comprise expressing the heavy chain and the light chains in a cell line comprising the nucleotide sequences encoding the heavy and light chains with a signal peptide. Host cells comprising these nucleotide sequences are encompassed herein.

Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2, and/or CH3). The sequences of human heavy chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, for example, an IgG1 region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see, e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence $(Gly_4\text{-}Ser)_3$, such that the VH and VL sequences can be expressed as a contiguous single-chain protein, with the VL and VH regions joined by the flexible linker (see, e.g., Bird et al., (1988) *Science* 242:423-426; Huston et al., (1988) *Proc. Natl. Acad. Sci. USA* 85:5879-5883; McCafferty et al., (1990) *Nature* 348:552-554).

II.D. Vectors

Certain aspects of the present disclosure are directed to vectors comprising a nucleic acid molecule disclosed herein. In some aspects, the vector is a viral vector. In some aspects, the vector is a viral particle or a virus. In some aspects, the vector is a mammalian vector. In some aspects, the vector is a bacterial vector.

In certain aspects, the vector is a retroviral vector. In some aspects, the vector is selected from the group consisting of an adenoviral vector, a lentivirus, a Sendai virus, a baculoviral vector, an Epstein Barr viral vector, a papovaviral vector, a vaccinia viral vector, a herpes simplex viral vector, and an adeno associated virus (AAV) vector. In particular aspects, the vector is an AAV vector. In some aspects, the vector is a lentivirus. In particular aspects, the vector is an AAV vector. In some aspects, the vector is a Sendai virus. In some aspects, the vector is a hybrid vector. Examples of hybrid vectors that can be used in the present disclosure can be found in Huang and Kamihira, *Biotechnol. Adv.* 31(2): 208-23 (2103), which is incorporated by reference herein in its entirety.

In some aspects, the vector further comprises one or more regulatory elements. Regulatory elements useful in the vectors disclosed herein include, but are not limited to, promoters, enhancers, polyA sequences, miRNA binding sequences, intronic sequences, splice acceptor sites, and any combination thereof. In some aspects, the vector comprises a tissue specific promoter. In some aspects, the vector comprises a tissue specific enhancer.

II.E. Pharmaceutical Compositions

Certain aspects of the present disclosure are directed to pharmaceutical compositions comprising an anti-FLC antibody disclosed herein and a pharmaceutically acceptable excipient. Some aspects of the present disclosure are directed to pharmaceutical compositions comprising a nucleic acid molecule encoding an anti-FLC antibody disclosed herein and a pharmaceutically acceptable excipient. Some aspects of the present disclosure are directed to pharmaceutical compositions comprising a vector or a set of vectors disclosed herein and a pharmaceutically acceptable excipient.

In some aspects, the composition of the disclosure further comprises a bulking agent. A bulking agent can be selected from the group consisting of NaCl, mannitol, glycine, alanine, and any combination thereof. In other aspects, the composition of the disclosure comprises a stabilizing agent. The stabilizing agent can be selected from the group consisting of sucrose, trehalose, raffinose, arginine; or any combination thereof. In other aspects, the composition of the disclosure comprises a surfactant. The surfactant can be selected from the group consisting of polysorbate 80 (PS80), polysorbate 20 (PS20), and any combination thereof. In certain aspects, the composition further comprises a chelating agent. The chelating agent can be selected from the group consisting of diethylenetriaminepentaacetic acid (DTPA), ethylenediaminetetraacetic acid, nitrilotriacetic acid, and any combination thereof. A pharmaceutical composition may comprise the antibodies described herein solubilized in appropriate isotonic buffer such as 0.9% NaCl or 5% glucose and may comprise other surfactants, pH buffers, or antioxidants.

In one aspect, the composition further comprises NaCl, mannitol, pentetic acid (DTPA), sucrose, PS80, and any combination thereof.

As used herein, "pharmaceutically acceptable carrier" includes any and all solvents, dispersion media, coatings, antibacterial and antifungal agents, isotonic and absorption delaying agents, and the like that are physiologically compatible. In some aspects, the carrier is suitable for intravenous, intramuscular, subcutaneous, parenteral, spinal or epidermal administration (e.g., by injection or infusion). Depending on the route of administration, the active compound, i.e., antibody, can be coated in a material to protect the compound from the action of acids and other natural conditions that can inactivate the compound.

The pharmaceutical compounds described herein can include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein can also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that can be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of presence of microorganisms can be ensured both by sterilization procedures, supra, and by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition can comprise a preservative or can be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, the compositions can include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

A composition described herein can be formulated for administration via one or more routes. In some aspects, the pharmaceutical composition is formulated for intravenous, intramuscular, intradermal, intraperitoneal, subcutaneous, spinal or other parenteral administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In some aspects, the pharmaceutical composition is formulated a non-parenteral route of administration, such as a topical, epidermal or mucosal route of administration, for example, intranasally, orally, vaginally, rectally, sublingually or topically.

The anti-FLC antibodies can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In some aspects, the anti-FLC antibodies described herein are formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes can comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J. Physiol.* 1233: 134); p120 (Schreier et al. (1994) *J. Biol. Chem.* 269:9090); see also K. Keinanen; M. L. Laukkanen (1994) *FEBS Lett.* 346: 123; J. J. Killion; I. J. Fidler (1994) *Immunomethods* 4:273.

III. Methods of Use

The anti-FLC antibodies used herein can be used for any purpose. Certain aspects of the present disclosure are directed to methods of measuring FLC in a sample. Other aspects of the present disclosure are directed to methods of treating a disease or condition in a subject in need thereof. In some aspects, the anti-FLC antibody is modified and/or formulated, e.g., as described herein, for a particular use.

III.A. Methods of Measuring

Certain aspects of the present disclosure are directed to methods of measuring light chain immunoglobulins. The antibodies disclosed herein can be used to measure any immunoglobulin light chain or aggregate thereof. In some aspects, the anti-FLC antibodies are used to measure an immunoglobulin light chain or an aggregate thereof in vivo. In some aspects, the anti-FLC antibodies are used to measure an immunoglobulin light chain or an aggregate thereof in a biological sample collected from a subject. In some aspects, the biological sample is a plasma sample, a blood sample, a tissue sample (e.g., a tissue biopsy), a urine sample, or any combination thereof.

In some aspects, the method comprises measuring light chain fibrils. As such, the antibodies described herein can be used to identify a subject that has a disease or condition characterized by the formation of immunoglobulin light chain deposits, e.g., amyloid fibril deposits. In some aspects, the anti-FLC antibodies are used to identify (e.g., diagnose) a subject as having an amyloidosis. In some aspects, the anti-FLC antibodies are used to identify a subject as having a systemic amyloidosis. In some aspects, the anti-FLC antibodies are used to identify a subject as having an AL amyloidosis. In some aspects, the anti-FLC antibodies are used to identify a subject as having a plasma cell dyscrasias. In some aspects, the anti-FLC antibodies are used to identify a subject as having a monoclonal gammopathy of unknown significance (MGUS). In some aspects, the anti-FLC antibodies are used to identify a subject as having multiple myeloma (MM). In some aspects, the anti-FLC antibodies are used to identify a subject as having plasma cell leukemia (PCL).

In some aspects, the anti-FLC antibody comprises one or more label. Any label known in the art can be used to increase the ability of the anti-FLC to be detected and/or visualized. In some aspects, the label comprises a chemical label. In some aspects, the label comprises an enzymatic label. In some aspects, label comprises a substrate, which is detectable in the presence of a particular enzyme. In some aspects, the label is a fluorescent label.

Certain aspects of the present disclosure are directed to methods of measuring light chain immunoglobulins in vivo using an anti-FLC antibody disclosed herein. In some aspects, the anti-FLC antibody comprises a detectable probe. In some aspects, the anti-FLC antibody is a contrast-conjugated antibody. In some aspects, the method is a diagnostic medical imaging method, e.g., a PET/CT, SPECT, MRI, or any combination thereof.

III.B. Methods of Treatment

Certain aspects of the present disclosure are directed to methods of treating a disease or condition in a subject in need thereof, comprising administering an anti-FLC antibody disclosed herein. In some aspects, the disease or condition comprises an amyloidosis. In some aspects, the disease or condition comprises a systemic amyloidosis. In some aspects, the disease or condition comprises an AL amyloidosis. In some aspects, the disease or condition comprises a plasma cell dyscrasias. In some aspects, the disease or condition comprises a monoclonal gammopathy of unknown significance (MGUS). In some aspects, the disease or condition comprises multiple myeloma (MM). In some aspects, the disease or condition comprises plasma cell leukemia (PCL).

Certain aspects of the present disclosure are directed to methods of reducing and/or clearing an immunoglobulin light chain aggregate, e.g., an amyloid fibril, in a subject in need thereof, comprising administering an anti-FLC antibody disclosed herein. In some aspects, the subject has one or more immunoglobulin light chain aggregate, e.g., amyloid fibril, in the heart. In some aspects, the subject has one or more immunoglobulin light chain aggregate, e.g., amyloid fibril, in a kidney. In some aspects, the subject has one or more immunoglobulin light chain aggregate, e.g., amyloid fibril, in a tissue of the nervous system. In some aspects, the subject has one or more immunoglobulin light chain aggregate, e.g., amyloid fibril, in the brain.

Certain aspects of the present disclosure are directed to methods of treating a nephrotic syndrome in a subject in need thereof, comprising administering to the subject an anti-FLC antibody disclosed herein, wherein the nephrotic syndrome comprises one or more immunoglobulin light chain deposit, e.g., one or more amyloid fibril deposit. Certain aspects of the present disclosure are directed to methods of treating a hepatomegaly in a subject in need thereof, comprising administering to the subject an anti-FLC antibody disclosed herein, wherein the hepatomegaly comprises one or more immunoglobulin light chain deposit, e.g., one or more amyloid fibril deposit. Certain aspects of the present disclosure are directed to methods of treating a peripheral neuropathy in a subject in need thereof, comprising administering to the subject an anti-FLC antibody disclosed herein, wherein the peripheral neuropathy comprises one or more immunoglobulin light chain deposit, e.g., one or more amyloid fibril deposit. Certain aspects of the present disclosure are directed to methods of treating a restrictive cardiomyopathy in a subject in need thereof, comprising administering to the subject an anti-FLC antibody disclosed herein, wherein the restrictive cardiomyopathy comprises one or more immunoglobulin light chain deposit, e.g., one or more amyloid fibril deposit.

In some aspects, administering the anti-FLC antibody to the subject results in the reduction and/or clearance of one or more immunoglobulin light chain aggregate, e.g., amyloid fibril, in the subject. In some aspects, the size of an immunoglobulin light chain aggregate, e.g., amyloid fibril, in the subject is reduced following administration of the anti-FLC antibody. In some aspects, the size of the immunoglobulin light chain aggregate, e.g., amyloid fibril, in the subject is reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or at least about 99%, following administration of the anti-FLC antibody. In some aspects, the immunoglobulin light chain aggregate, e.g., amyloid fibril, is completely dissociated or otherwise cleared from the subject following administration of the anti-FLC antibody.

In some aspects, administering the anti-FLC antibody to the subject results in the reduced or slowed formation of one or more immunoglobulin light chain aggregate, e.g., amyloid fibril, in the subject. In some aspects, the rate of immunoglobulin light chain aggregate formation, e.g., amyloid fibril formation, in the subject is reduced following administration of the anti-FLC antibody. In some aspects, the size of the immunoglobulin light chain aggregate, e.g., amyloid fibril, in the subject is reduced by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 95%, or at least about 99%, following administration of the anti-FLC antibody. In some aspects, the rate of immunoglobulin light chain aggregate formation, e.g., amyloid fibril formation, in the subject is halted, e.g., no further immunoglobulin light chain aggregate formation, following administration of the anti-FLC antibody.

In some aspects, the anti-FLC antibody induces an immune response in the subject following administration. In some aspects, the anti-FLC antibody opsonizes an immunoglobulin light chain, e.g., an immunoglobulin light chain aggregate, e.g., an amyloid fibril, in the subject. In some aspects, the immune response comprises induction of macrophages. In some aspects, the immune response comprises recruitment of macrophages. In some aspects, the immune response comprises increased phagocytosis of the immunoglobulin light chain, e.g., immunoglobulin light chain aggregate, e.g., amyloid fibril, in the subject. In some aspects, the immune response is increased by at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, at least about 10-fold, relative to the immune response prior to the administration of the anti-FLC antibody.

IV. Antibody Production

The anti-FLC antibodies described herein can be produced using a variety of known techniques, such as the standard somatic cell hybridization technique described by Kohler and Milstein, *Nature* 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

An example of an animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized anti-FLC antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see, e.g., U.S. Pat. No. 4,816,567 to Cabilly et al.). To create a humanized antibody, the murine CDR regions can be inserted into a human framework using methods known in the art (see, e.g., U.S. Pat. No. 5,225,539 to Winter, and U.S. Pat. Nos. 5,530,101; 5,585,089; 5,693, 762 and 6,180,370 to Queen et al).

In some aspects, the anti-FLC antibodies described herein are human monoclonal antibodies. Such human monoclonal antibodies directed against FLC can be generated using transgenic or transchromosomic mice carrying parts of the human immune system rather than the mouse system. These transgenic and transchromosomic mice include mice referred to herein as HuMAb mice (e.g., the HuM-Abmouse® (Medarex, Inc.)) and KM mice, respectively, and are collectively referred to herein as "human Ig mice."

In some aspects, the anti-FLC antibodies described herein are raised using a mouse that carries human immunoglobulin sequences on transgenes and transchomosomes, such as a mouse that carries a human heavy chain transgene and a human light chain transchromosome. Such mice, referred to herein as "KM mice," are described in detail in PCT Publication WO 02/43478 to Ishida et al.

Still further, alternative transgenic animal systems expressing human immunoglobulin genes are available in the art and can be used to raise anti-FLC antibodies described herein. For example, an alternative transgenic system referred to as the Xenomouse (Abgenix, Inc.) can be used; such mice are described in, for example, U.S. Pat. Nos. 6,075,181; 6,114,598; 6, 150,584 and 6,162,963 to Kucherlapati et al.

Moreover, alternative transchromosomic animal systems expressing human immunoglobulin genes are available in the art and can be used to raise anti-FLC antibodies described herein. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (Kuroiwa et al. (2002) *Nature Biotechnology* 20:889-894) and can be used to raise anti-FLC antibodies described herein.

Additional mouse systems described in the art for raising human antibodies, e.g., human anti-FLC antibodies, include (i) the VELOCLMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MEMO® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/ 0069614, WO 2011/072204, WO 2011/097603, WO 2011/ 163311, WO 2011/163314, WO 2012/148873, US 2012/ 0070861 and US 2012/0073004.

Human monoclonal anti-FLC antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal anti-FLC antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The nucleic acids encoding the antibodies described herein can be used to infect, transfect, transform, or otherwise render a suitable cell transgenic for the nucleic acid, thus enabling the production of antibodies for commercial or therapeutic uses. Standard cell lines and methods for the production of antibodies from a large scale cell culture are known in the art. See e.g., Li et al., "Cell culture processes for monoclonal antibody production."*Mabs.* 2010 September-October; 2(5): 466-477. In certain embodiments, the cell is a Eukaryotic cell. In certain embodiments, the Eukaryotic cell is a mammalian cell. In certain embodiments, the mammalian cell is a cell line useful for producing antibodies is a Chines Hamster Ovary cell (CHO) cell, an NSO murine myeloma cell, or a PER.C6® cell. In certain embodiments, the nucleic acid encoding the antibody is integrated into a genomic locus of a cell useful for producing antibodies. In certain embodiments, described herein is a method of making an antibody comprising culturing a cell comprising a nucleic acid encoding an antibody under conditions in vitro sufficient to allow production and secretion of said antibody.

In certain embodiments, described herein, is a master cell bank comprising: (a) a mammalian cell line comprising a nucleic acid encoding an antibody described herein integrated at a genomic location; and (b) a cryoprotectant. In certain embodiments, the cryoprotectant comprises glycerol or DMSO. In certain embodiments, the master cell bank comprises: (a) a CHO cell line comprising a nucleic acid encoding an antibody described herein integrated at a genomic location; and (b) a cryoprotectant. In certain embodiments, the cryoprotectant comprises glycerol or DMSO. In certain embodiments, the master cell bank is contained in a suitable vial or container able to withstand freezing by liquid nitrogen.

Also described herein are methods of making an antibody described herein. Such methods comprise incubating a cell or cell-line comprising a nucleic acid encoding the antibody in a cell culture medium under conditions sufficient to allow for expression and secretion of the antibody, and further harvesting the antibody from the cell culture medium. The harvesting can further comprise one or more purification steps to remove live cells, cellular debris, non-antibody proteins or polypeptides, undesired salts, buffers, and medium components. In certain embodiments, the additional purification step(s) include centrifugation, ultracentrifugation, protein A, protein G, protein A/G, or protein L purification, and/or ion exchange chromatography.

EXAMPLES

The following illustrative examples are representative of embodiments of compositions and methods described herein and are not meant to be limiting in any way.

Example 1: Generation of Antibodies

An epitope buried within the native LC structure was selected that contributes the same structural fold in both κ

(STYSLSSTLT (SEQ ID NO: 1)) and λ (NKYAASSYLSL (SEQ ID NO: 2)) light chain proteins. Epitopes were selected on the constant domains of light chains since the sequence is present in all AL patients, and would thus bind with less variability between patients compared to antibodies designed against the variable domains. Both antigens comprise inner strands of the two-layer β-sandwich motif of the immunoglobulin domain and are >85% buried in the natively folded dimer and monomer (FIG. 1A). The antigens are not involved in disulfide bond formation, and possess significant antigenicity as assessed by the EMBOSS explorer (Kolaskar et al., 1990). Because these antigens are buried in the native structures, antibodies raised to these antigens should not bind natively folded light chains.

Suitable peptide sequences (GKGGSTYSLSSTLTGGKG (SEQ ID NO: 3)

and

GKGGNKYAASSYLSLGGKG (SEQ ID NO: 4))

were then designed to raise antibodies that could potentially target only the pathological misfolded states of the AL protein while leaving the natively folded, normal immunoglobulin light chains untouched. These antibodies are referred to as the anti-κ antibody and the anti-λ antibody.

Figure 2A:
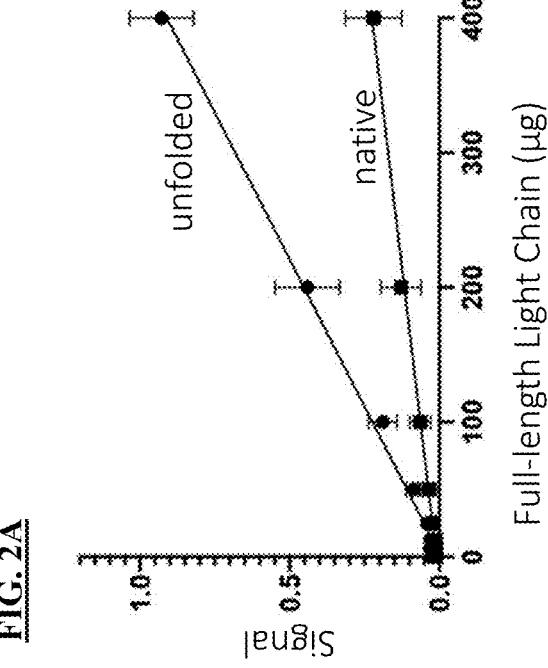
Figure 3B:
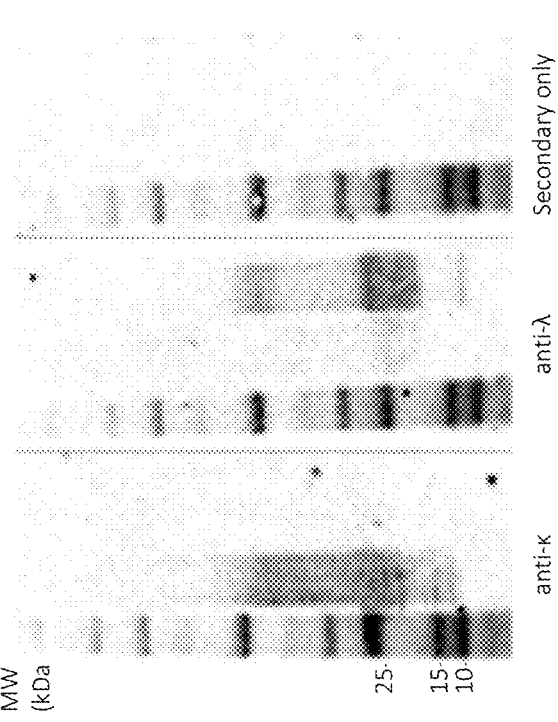
FIGS. 3A-3B show detection of unfolded full-length kappa light chain protein by denaturing western blot using kappa (KLC) and lambda (LLC) pooled light chains from myeloma plasma.
Figure 3A:
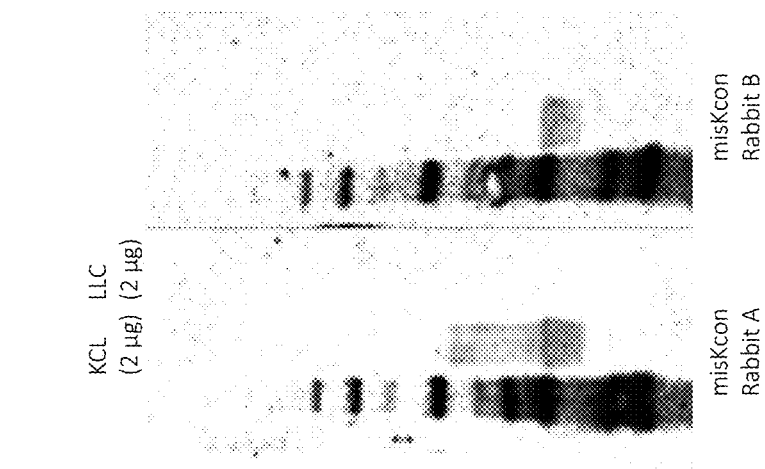

An FL-LC protein expression system was used to test the specificity of the anti-κ antibody against κ FL-LC in its denatured and native forms. An indirect ELISA assay showed the anti-κ antibody is specific for the unfolded form of the κ FL-LC protein (FIG. 2A). Pan-specific commercial antibodies, however detected no difference between folded and unfolded LC proteins. (FIG. 2B). The specificity of the anti-κ antibody was also confirmed using denaturing SDS-PAGE western blots with the anti-κ antibody (FIG. 3A) and commercial antibodies (FIG. 3B).

Figure 4:
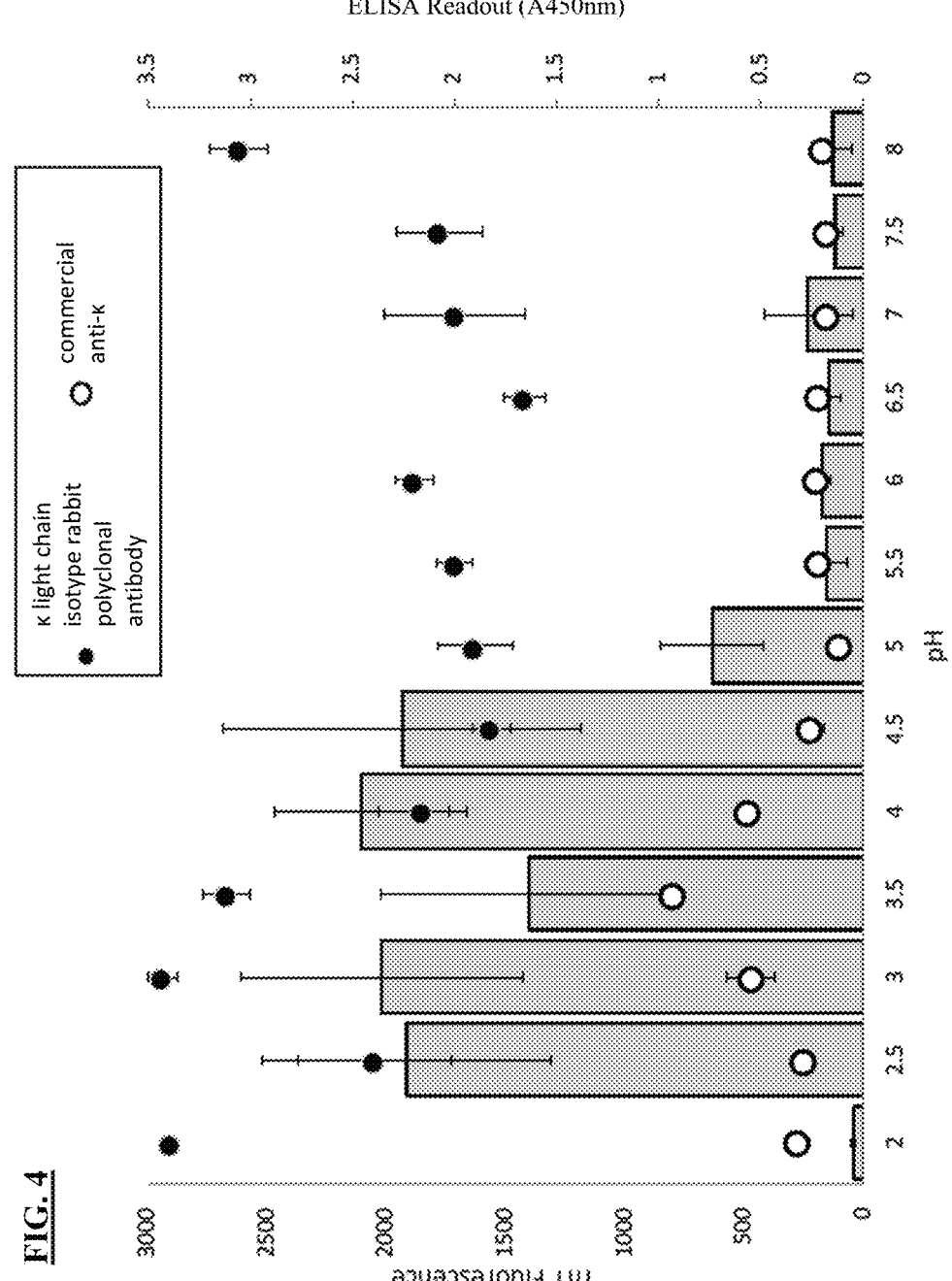
FIG. 4 is a plot of signal detected using a κ light chain isotype rabbit polyclonal antibody showing pH-dependent aggregate binding. Grey bars indicate relative ThT fluorescence at indicated pH (n=3, left y-axis), white circles indicate a κ light chain isotype rabbit polyclonal antibody ELISA readout showing a relationship between binding and aggregation (n=3, right y-axis), and black circles indicate a commercial anti-κ readout showing no pH-dependent relationship (n=3, right y-axis).

The ability of the anti-κ antibody to bind misfolded κ light chain aggregates in vitro was then tested using thioflavin T (ThT) fluorescence assays. The pH dependence of aggregation of κ light chains was measured. Increased aggregation propensity was shown between pH 2.5 and 5 (FIG. 4). The produced aggregates were then used to perform an ELISA with both the anti-κ antibody and a commercial pan-specific antibody. A correlation was observed between the amount of aggregates produced (ThT) and the binding of the anti-κ antibody but not the commercial antibody (FIG. 5). These results were verified through performance of immunogold electron microscopy (IGEM) on the aggregates. Briefly, 200-mesh copper grids were coated with aggregates at either pH 4.5 or pH 6, blocked, and probed with the anti-κ antibody. A gold-conjugated anti-rabbit secondary was used to allow for the visualization of 6 nm electron-opaque gold particles (black dots by EM). Binding of the anti-κ antibody to aggregates was observed at both pHs (FIGS. 5A-5C).

Example 2: Clearance of AL Aggregates In Vitro

Figures 6A, 6B:
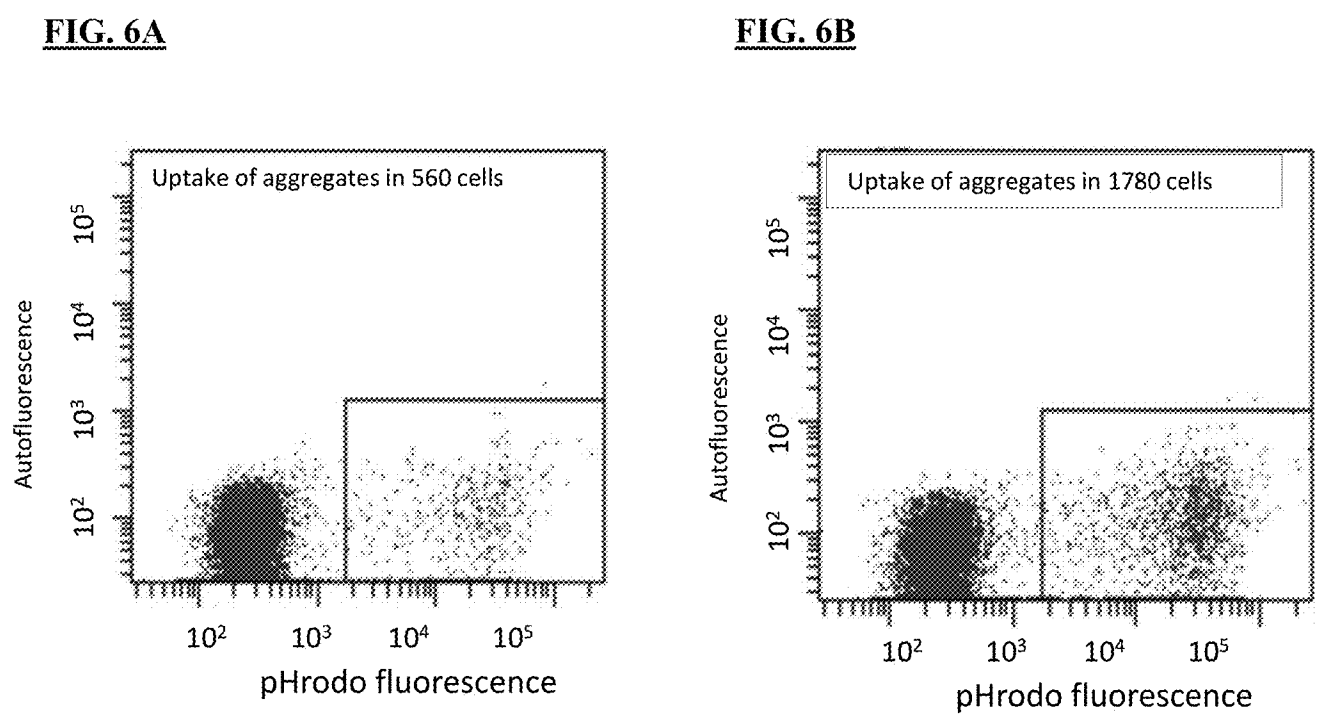

The ability of the anti-κ antibody to facilitate immune clearance of AL aggregates in vitro was tested through a phagocytosis assay. The assay was performed using THP-1 monocytic cells and light-chain aggregates labelled with pH-sensitive rhodamine (pHrodo) dye which fluoresces at a low pH. Aggregates were incubated either with (FIG. 6B) or without (FIG. 6A) the anti-κ antibody, and monocytic cells were added. The presence of intracellular pHrodo fluorescence is indicative of uptake of labelled aggregates and internalization to endolysosomes. Uptake of pHrodo was assessed by standard flow cytometry methods, gating on fluorescence intensity. A three-fold increase in monocytic cellular uptake was observed in the presence of the anti-κ antibody, indicating an effective clearance of immune complexes (FIGS. 6A-6B).

The specificity of the anti-κ antibody was also validated through immunohistochemistry using human cardiac tissue. The results indicate that the anti-κ antibody does not bind lambda light chain amyloid (FIGS. 7A-7J) or ATTR amyloid, another protein that forms cardiac amyloid (FIGS. 8A-8E).

Example 3: Immunoreactivity of the Anti-κ Antibody In Vivo

Figure 9:
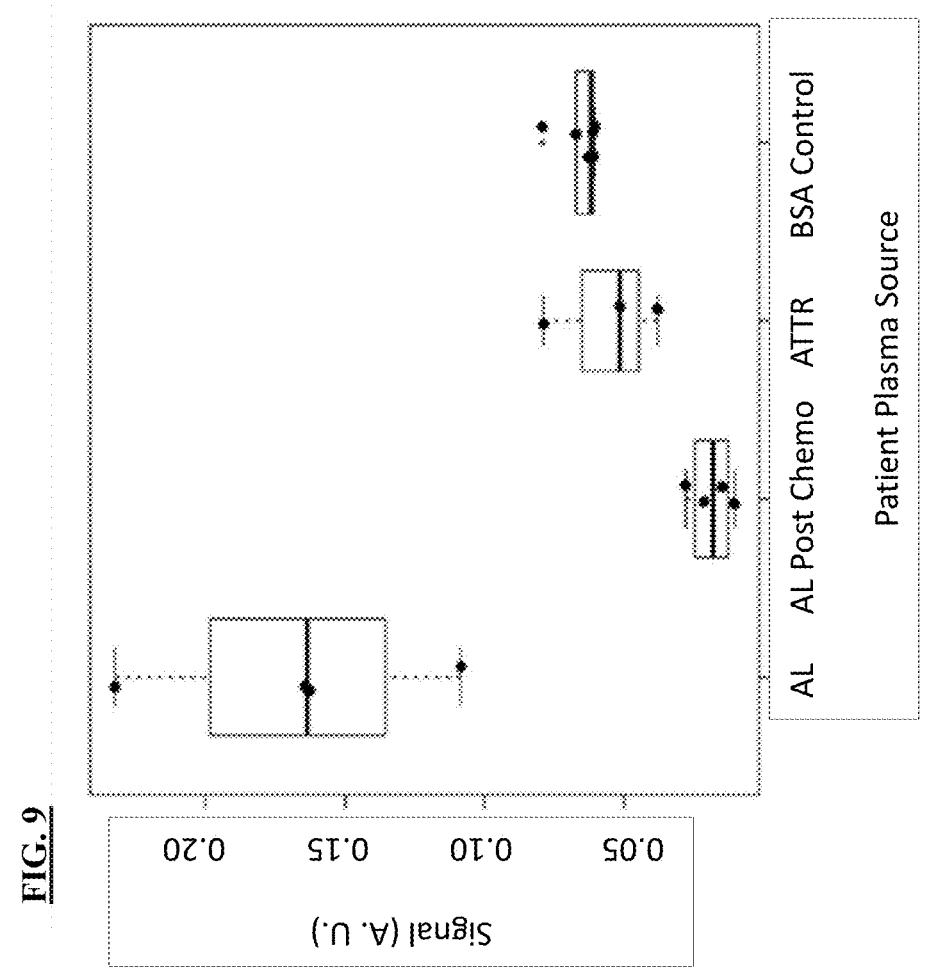
FIG. 9 is a box and whisker plot of a signal detected using indirect ELISA of various patient plasma samples using anti-$C_L$ antibody. Patient plasma with AL amyloidosis showed increased signal compared to an HFpEF control such as an ATTR amyloidosis patient.

An indirect ELISA assay was performed using plasma from patients with AL-CM to assess the immunoreactivity of the anti-κ antibody for AL species in vivo. The anti-κ antibody successfully distinguished patients with AL-CM from those who had been previously treated with anti-myeloma chemotherapy and non-AL cardiac amyloidosis patients (e.g., ATTR-CM) regardless of patient AL isotype (FIG. 9).

Example 4: Generation of an Anti-κ Monoclonal Antibody

The present examples describes the design and generation of an anti-κ monoclonal antibody. To generate antibodies against misfolded immunoglobulin light chain, we selected as the antigens two internal β-strands, one in the constant domain of the kappa light chain (STYSLSSTLT; SEQ ID NO: 1), residues 171-180 of SEQ ID NO: 5, and the second in the constant domain of the lambda light chain (NKYAAS-SYLSL; SEQ ID NO: 2), residues 174-184 of SEQ ID NO: 7, as described in Example 1.

Additional residues were added to these epitopes to generate antigenic peptides (acetyl-CGKGGSTYSLSSTLTGGKG-amide; SEQ ID NO: 3, and acetyl-CGGNKYAASSYLSLGG-amide; SEQ ID NO: 9).

These peptides were then covalently coupled to the surface of keyhole limpet hemocyanin, through the side chain of the N-terminal Cys residue and maleimide chemistry. The peptide conjugates were used as immunogen to raise antibodies that could potentially target only the pathological misfolded states of the light chain protein while leaving the natively folded, normal immunoglobulin light chains untouched. Monoclonal antibodies were produced through mouse hybridoma technology.

Among several monoclonal antibodies generated using the κ antigenic peptide (SEQ ID NO: 1) in mice via hybridoma technology, one hybridoma clone was identified that produces an antibody (termed herein as LX-96) possessing optimal misfolding-specific binding properties. This hybridoma cell contains DNA sequences encoding for heavy (FIG. 10C) and light chains (FIG. 10D) of the antibody, with the amino acid sequences annotated in FIGS. 10A-10B. Analysis of the constant domain suggests that the antibody is of the IgG1/κ subclass, while sequence analysis of the variable domains reveal unique CDR sequences (Table 3 and 4). These 6 CDR sequences give LX-96 its properties of binding misfolded and aggregated forms of κ light chain, while evading the native conformation.

TABLE 3

| Amino acid sequence of LX-96 light chain variable domain (SEQ ID NO: 10) | | | | |
|---|---|---|---|---|
| Kabat # | Chothia # | Linear # | FR/CDR | AA |
| 1 | 1 | 1 | FR1 | D |
| 2 | 2 | 2 | FR1 | V |
| 3 | 3 | 3 | FR1 | V |
| 4 | 4 | 4 | FR1 | M |
| 5 | 5 | 5 | FR1 | T |
| 6 | 6 | 6 | FR1 | Q |
| 7 | 7 | 7 | FR1 | T |
| 8 | 8 | 8 | FR1 | P |
| 9 | 9 | 9 | FR1 | L |
| 10 | 10 | 10 | FR1 | T |
| 11 | 11 | 11 | FR1 | L |
| 12 | 12 | 12 | FR1 | S |
| 13 | 13 | 13 | FR1 | V |
| 14 | 14 | 14 | FR1 | T |
| 15 | 15 | 15 | FR1 | V |
| 16 | 16 | 16 | FR1 | G |
| 17 | 17 | 17 | FR1 | Q |
| 18 | 18 | 18 | FR1 | P |
| 19 | 19 | 19 | FR1 | A |
| 20 | 20 | 20 | FR1 | S |
| 21 | 21 | 21 | FR1 | I |
| 22 | 22 | 22 | FR1 | S |
| 23 | 23 | 23 | FR1 | C |
| 24 | 24 | 24 | CDR-L1 | K |
| 25 | 25 | 25 | CDR-L1 | S |
| 26 | 26 | 26 | CDR-L1 | S |
| 27 | 27 | 27 | CDR-L1 | Q |
| 27A | 28 | 28 | CDR-L1 | S |
| 27B | 29 | 29 | CDR-L1 | L |
| 27C | 30 | 30 | CDR-L1 | L |
| 27D | 30A | 31 | CDR-L1 | D |
| 27E | 30B | 32 | CDR-L1 | G |
| 28 | 30C | 33 | CDR-L1 | D |
| 29 | 30D | 34 | CDR-L1 | G |
| 30 | 30E | 35 | CDR-L1 | K |
| 31 | 31 | 36 | CDR-L1 | T |
| 32 | 32 | 37 | CDR-L1 | Y |
| 33 | 33 | 38 | CDR-L1 | L |
| 34 | 34 | 39 | CDR-L1 | N |
| 35 | 35 | 40 | FR2 | W |
| 36 | 36 | 41 | FR2 | L |
| 37 | 37 | 42 | FR2 | L |
| 38 | 38 | 43 | FR2 | Q |
| 39 | 39 | 44 | FR2 | R |
| 40 | 40 | 45 | FR2 | P |
| 41 | 41 | 46 | FR2 | G |
| 42 | 42 | 47 | FR2 | Q |
| 43 | 43 | 48 | FR2 | S |
| 44 | 44 | 49 | FR2 | P |
| 45 | 45 | 50 | FR2 | K |
| 46 | 46 | 51 | FR2 | R |
| 47 | 47 | 52 | FR2 | L |
| 48 | 48 | 53 | FR2 | I |
| 49 | 49 | 54 | FR2 | Y |
| 50 | 50 | 55 | CDR-L2 | L |
| 51 | 51 | 56 | CDR-L2 | V |
| 52 | 52 | 57 | CDR-L2 | S |
| 53 | 53 | 58 | CDR-L2 | K |
| 54 | 54 | 59 | CDR-L2 | L |
| 55 | 55 | 60 | CDR-L2 | D |
| 56 | 56 | 61 | CDR-L2 | S |
| 57 | 57 | 62 | FR3 | G |
| 58 | 58 | 63 | FR3 | V |
| 59 | 59 | 64 | FR3 | P |
| 60 | 60 | 65 | FR3 | D |
| 61 | 61 | 66 | FR3 | R |
| 62 | 62 | 67 | FR3 | F |
| 63 | 63 | 68 | FR3 | T |
| 64 | 64 | 69 | FR3 | G |
| 65 | 65 | 70 | FR3 | S |
| 66 | 66 | 71 | FR3 | G |

TABLE 3-continued

| | Amino acid sequence of LX-96 light chain variable domain (SEQ ID NO: 10) | | | |
|---|---|---|---|---|
| Kabat # | Chothia # | Linear # | FR/CDR | AA |
| 67 | 67 | 72 | FR3 | S |
| 68 | 68 | 73 | FR3 | G |
| 69 | 69 | 74 | FR3 | T |
| 70 | 70 | 75 | FR3 | D |
| 71 | 71 | 76 | FR3 | F |
| 72 | 72 | 77 | FR3 | T |
| 73 | 73 | 78 | FR3 | L |
| 74 | 74 | 79 | FR3 | K |
| 75 | 75 | 80 | FR3 | I |
| 76 | 76 | 81 | FR3 | S |
| 77 | 77 | 82 | FR3 | R |
| 78 | 78 | 83 | FR3 | V |
| 79 | 79 | 84 | FR3 | E |
| 80 | 80 | 85 | FR3 | A |
| 81 | 81 | 86 | FR3 | E |
| 82 | 82 | 87 | FR3 | D |
| 83 | 83 | 88 | FR3 | L |
| 84 | 84 | 89 | FR3 | G |
| 85 | 85 | 90 | FR3 | I |
| 86 | 86 | 91 | FR3 | Y |
| 87 | 87 | 92 | FR3 | Y |
| 88 | 88 | 93 | FR3 | C |
| 89 | 89 | 94 | CDR-L3 | W |
| 90 | 90 | 95 | CDR-L3 | Q |
| 91 | 91 | 96 | CDR-L3 | G |
| 92 | 92 | 97 | CDR-L3 | T |
| 93 | 93 | 98 | CDR-L3 | H |
| 94 | 94 | 99 | CDR-L3 | F |
| 95 | 95 | 100 | CDR-L3 | P |
| 96 | 96 | 101 | CDR-L3 | Q |
| 97 | 97 | 102 | CDR-L3 | T |
| 98 | 98 | 103 | FR4 | F |
| 99 | 99 | 104 | FR4 | G |
| 100 | 100 | 105 | FR4 | G |
| 101 | 101 | 106 | FR4 | G |
| 102 | 102 | 107 | FR4 | T |
| 103 | 103 | 108 | FR4 | K |
| 104 | 104 | 109 | FR4 | L |
| 105 | 105 | 110 | FR4 | E |
| 106 | 106 | 111 | FR4 | I |
| 107 | 107 | 112 | FR4 | K |

TABLE 4

| | Amino acid sequence of LX-96 heavy chain variable domain (SEQ ID NO: 14) | | | |
|---|---|---|---|---|
| Kabat # | Chothia # | Linear # | FR/CDR | AA |
| 1 | 1 | 1 | FR1 | Q |
| 2 | 2 | 2 | FR1 | V |
| 3 | 3 | 3 | FR1 | Q |
| 4 | 4 | 4 | FR1 | L |
| 5 | 5 | 5 | FR1 | Q |
| 6 | 6 | 6 | FR1 | Q |
| 7 | 7 | 7 | FR1 | P |
| 8 | 8 | 8 | FR1 | G |
| 9 | 9 | 9 | FR1 | A |
| 10 | 10 | 10 | FR1 | E |
| 11 | 11 | 11 | FR1 | L |
| 12 | 12 | 12 | FR1 | A |
| 13 | 13 | 13 | FR1 | R |
| 14 | 14 | 14 | FR1 | P |
| 15 | 15 | 15 | FR1 | G |
| 16 | 16 | 16 | FR1 | A |
| 17 | 17 | 17 | FR1 | S |
| 18 | 18 | 18 | FR1 | V |
| 19 | 19 | 19 | FR1 | K |
| 20 | 20 | 20 | FR1 | L |
| 21 | 21 | 21 | FR1 | S |
| 22 | 22 | 22 | FR1 | C |
| 23 | 23 | 23 | FR1 | K |

TABLE 4-continued

| | Amino acid sequence of LX-96 heavy chain variable domain (SEQ ID NO: 14) | | | |
|---|---|---|---|---|
| Kabat # | Chothia # | Linear # | FR/CDR | AA |
| 24 | 24 | 24 | FR1 | A |
| 25 | 25 | 25 | FR1 | S |
| 26 | 26 | 26 | FR1 | G |
| 27 | 27 | 27 | FR1 | Y |
| 28 | 28 | 28 | FR1 | T |
| 29 | 29 | 29 | FR1 | F |
| 30 | 30 | 30 | FR1 | T |
| 31 | 31 | 31 | CDR-H1 | S |
| 32 | 32 | 32 | CDR-H1 | F |
| 33 | 33 | 33 | CDR-H1 | W |
| 34 | 34 | 34 | CDR-H1 | I |
| 35 | 35 | 35 | CDR-H1 | Q |
| 36 | 36 | 36 | FR2 | W |
| 37 | 37 | 37 | FR2 | I |
| 38 | 38 | 38 | FR2 | K |
| 39 | 39 | 39 | FR2 | Q |
| 40 | 40 | 40 | FR2 | R |
| 41 | 41 | 41 | FR2 | P |
| 42 | 42 | 42 | FR2 | G |
| 43 | 43 | 43 | FR2 | Q |
| 44 | 44 | 44 | FR2 | G |
| 45 | 45 | 45 | FR2 | L |
| 46 | 46 | 46 | FR2 | E |
| 47 | 47 | 47 | FR2 | W |
| 48 | 48 | 48 | FR2 | I |
| 49 | 49 | 49 | FR2 | G |
| 50 | 50 | 50 | CDR-H2 | S |
| 51 | 51 | 51 | CDR-H2 | I |
| 52 | 52 | 52 | CDR-H2 | Y |
| 52A | 52A | 53 | CDR-H2 | P |
| 53 | 53 | 54 | CDR-H2 | G |
| 54 | 54 | 55 | CDR-H2 | D |
| 55 | 55 | 56 | CDR-H2 | G |
| 56 | 56 | 57 | CDR-H2 | D |
| 57 | 57 | 58 | CDR-H2 | T |
| 58 | 58 | 59 | CDR-H2 | R |
| 59 | 59 | 60 | CDR-H2 | Y |
| 60 | 60 | 61 | CDR-H2 | I |
| 61 | 61 | 62 | CDR-H2 | Q |
| 62 | 62 | 63 | CDR-H2 | K |
| 63 | 63 | 64 | CDR-H2 | F |
| 64 | 64 | 65 | CDR-H2 | R |
| 65 | 65 | 66 | CDR-H2 | G |
| 66 | 66 | 67 | FR3 | K |
| 67 | 67 | 68 | FR3 | A |
| 68 | 68 | 69 | FR3 | T |
| 69 | 69 | 70 | FR3 | L |
| 70 | 70 | 71 | FR3 | T |
| 71 | 71 | 72 | FR3 | A |
| 72 | 72 | 73 | FR3 | D |
| 73 | 73 | 74 | FR3 | E |
| 74 | 74 | 75 | FR3 | S |
| 75 | 75 | 76 | FR3 | S |
| 76 | 76 | 77 | FR3 | S |
| 77 | 77 | 78 | FR3 | T |
| 78 | 78 | 79 | FR3 | A |
| 79 | 79 | 80 | FR3 | Y |
| 80 | 80 | 81 | FR3 | M |
| 81 | 81 | 82 | FR3 | Q |
| 82 | 82 | 83 | FR3 | L |
| 82A | 82A | 84 | FR3 | S |
| 82B | 82B | 85 | FR3 | S |
| 82C | 82C | 86 | FR3 | L |
| 83 | 83 | 87 | FR3 | A |
| 84 | 84 | 88 | FR3 | S |
| 85 | 85 | 89 | FR3 | E |
| 86 | 86 | 90 | FR3 | D |
| 87 | 87 | 91 | FR3 | S |
| 88 | 88 | 92 | FR3 | A |
| 89 | 89 | 93 | FR3 | I |
| 90 | 90 | 94 | FR3 | Y |
| 91 | 91 | 95 | FR3 | Y |
| 92 | 92 | 96 | FR3 | C |
| 93 | 93 | 97 | FR3 | A |
| 94 | 94 | 98 | FR3 | I |

TABLE 4-continued

| | Amino acid sequence of LX-96 heavy chain variable domain (SEQ ID NO: 14) | | | |
|---|---|---|---|---|
| Kabat # | Chothia # | Linear # | FR/CDR | AA |
| 95 | 95 | 99 | CDR-H3 | V |
| 96 | 96 | 100 | CDR-H3 | T |
| 97 | 97 | 101 | CDR-H3 | T |
| 98 | 98 | 102 | CDR-H3 | A |
| 99 | 99 | 103 | CDR-H3 | P |
| 100 | 100 | — | — | — |
| 101 | 101 | 104 | CDR-H3 | D |
| 102 | 102 | 105 | CDR-H3 | Y |
| 103 | 103 | 106 | FR4 | W |
| 104 | 104 | 107 | FR4 | G |
| 105 | 105 | 108 | FR4 | Q |
| 106 | 106 | 109 | FR4 | G |
| 107 | 107 | 110 | FR4 | T |
| 108 | 108 | 111 | FR4 | T |
| 109 | 109 | 112 | FR4 | L |
| 110 | 110 | 113 | FR4 | T |
| 111 | 111 | 114 | FR4 | V |
| 112 | 112 | 115 | FR4 | S |
| 113 | 113 | 116 | FR4 | S |

Example 5: Characterization of Anti-κ Monoclonal Antibody

Figures 11A, 11B, 11C:
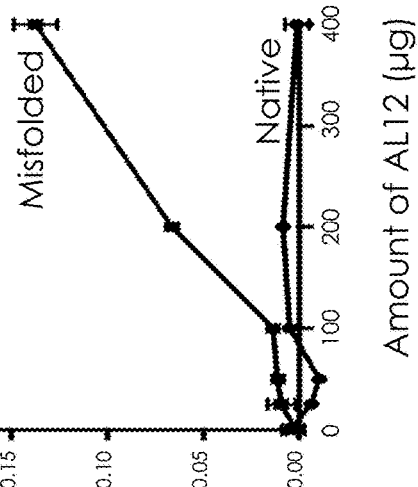
FIGS. 11A-11C are line graphs illustrating the results of indirect ELISA using LX-96 (FIG. 11A) or commercial control antibodies (FIG. 11B) to detect native or misfolded forms of kappa light chain. Varying concentrations of native or misfolded AL09 were bound by LX-96 (FIG. 11A) or commercial controls (FIG. 11B) and detected using appropriate HRP-conjugated secondary antibodies using TMB chemistry.
Figure 12:
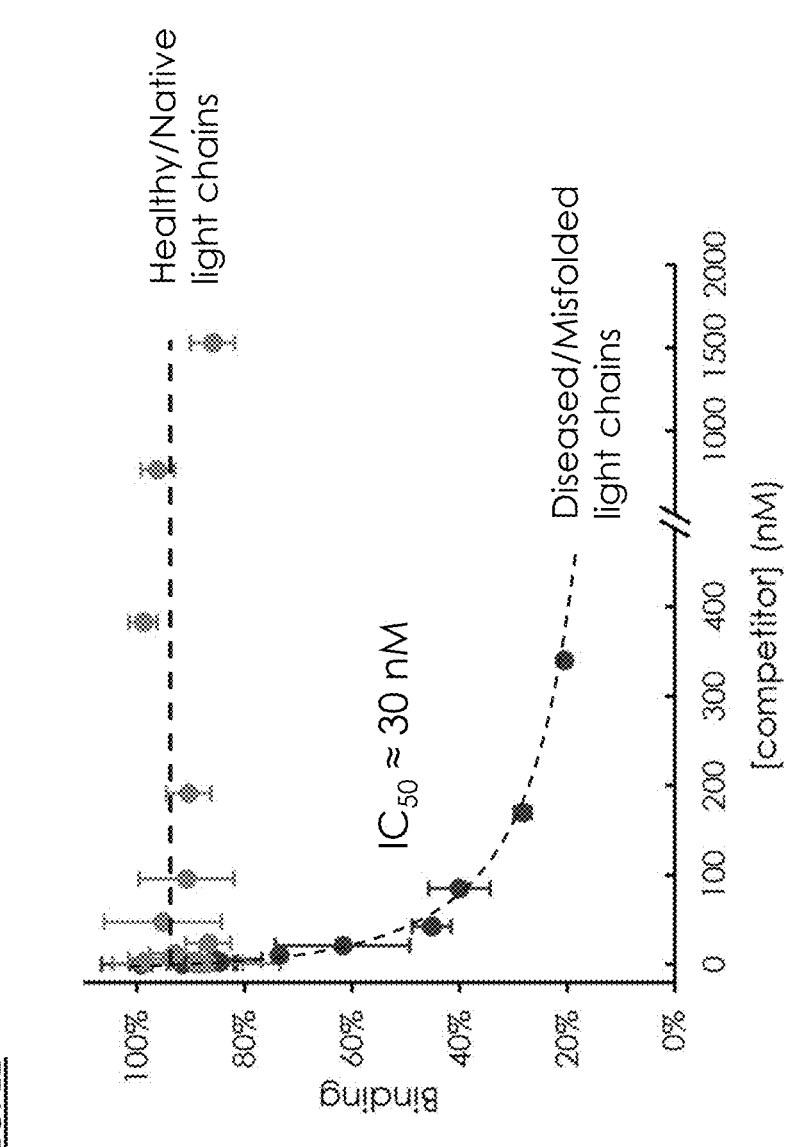
FIG. 12 is a graphical representation of results of competition ELISA using misfolded or native AL09 as competitors for LX-96 binding. Binding is presented as a percentage, where 100% represents maximum binding between LX-96 and adsorbed AL09 (no competition). Increasing concentrations of misfolded AL09 competitor successfully competed for LX-96 binding (bottom/black), while native AL09 demonstrated no competition (top/grey).

To validate the binding specificity of LX-96 for non-native, misfolded/unfolded kappa light chains only, we performed immunochemical assays using the AL disease-associated kappa light chain variants (AL09 or AL12), expressed and purified from T7 SHuffle cells (New England Biolabs). Using an indirect ELISA we show that LX-96 has strong binding affinity for both misfolded/unfolded kappa light chain variants, which was produced by unfolding AL09 or AL12 in 6M guanidine hydrochloride followed by reduction in dithiothreitol and alkylation with iodoacetamide, but not for natively folded kappa light chains (FIGS. 11A and 11C). This binding activity contrasts with the commercial anti-kappa light chain antibody (Agilent DAKO) that cannot distinguish between native and misfolded/unfolded AL09 (FIG. 11B). Competition ELISA was performed to obtain a measure of the relative binding affinity of LX-96 for misfolded versus native kappa light chains. Misfolded AL09 was coated in a 96-well plate and a mixture of LX-96 and competitor was added during primary antibody binding. Misfolded AL09 competed effectively for binding to LX-96 with an inhibition constant ($IC_{50}$) of 30 nM (FIG. 12) indicating strong binding affinity. Natively folded kappa light chains, on the other hand, did not show any measurable competition for binding, indicating that LX-96 has specific binding towards misfolded light chains and not to natively folded light chains.

Figures 13A, 13B:
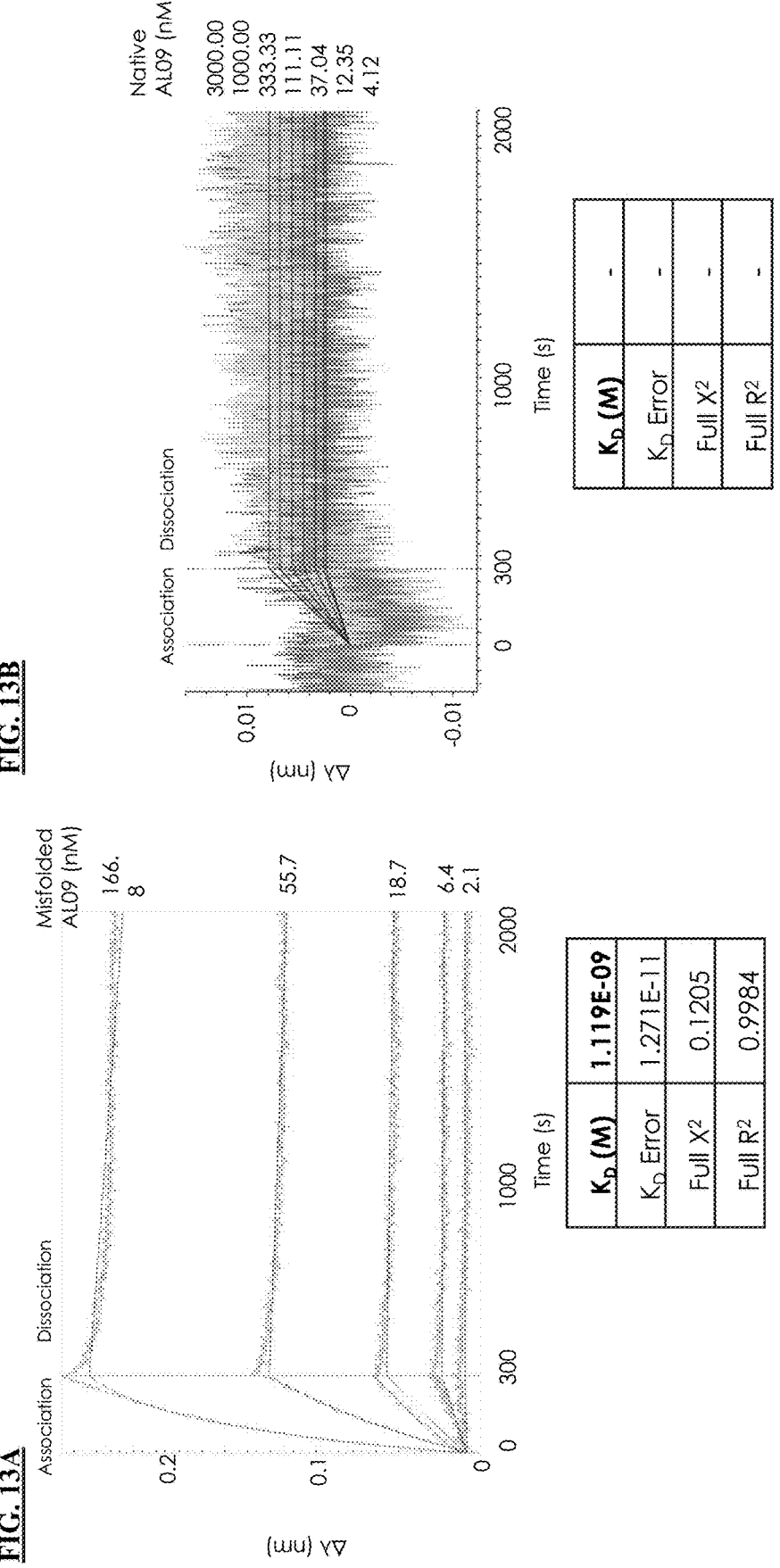
FIGS. 13A-13D are bio-layer interferometry sensorgrams of binding interactions between LX-96 and misfolded (FIG. 13A, 13C) or native kappa light chain variants (FIG. 13B, 13D). Binding of LX-96 with its targets at a range of target concentrations was measured by changes in wavelength (nm) over 2000 seconds (300 s association, 1700 s dissociation). Association and dissociation curves were fit using Octet Systems Software to determine KD, KD Error, X2 and R2 values (table insets.
Figures 13C, 13D:
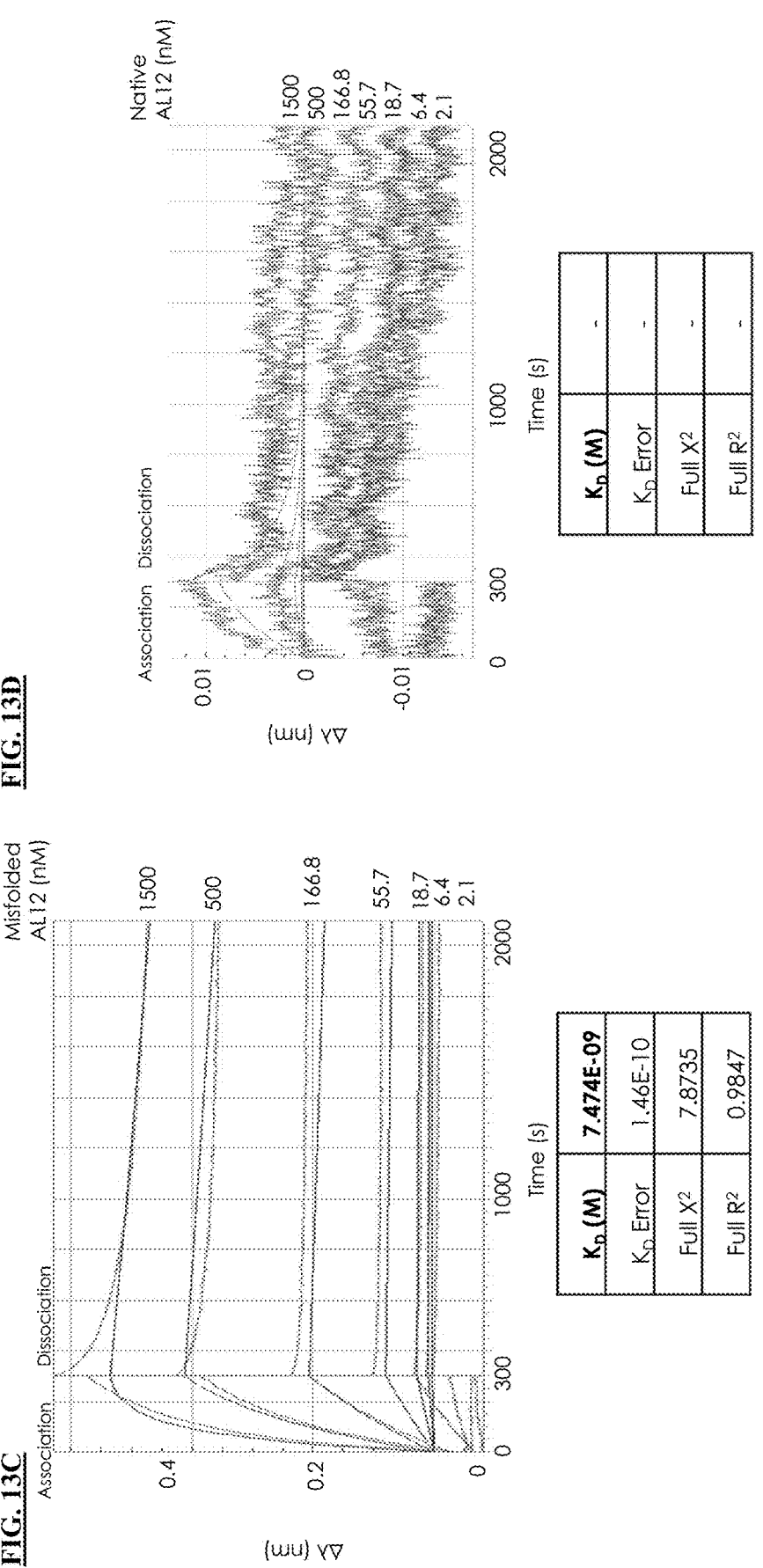

Example 6: Quantification of Binding Affinity (KD) Using Bio-Layer Interferometry We quantified the monovalent binding affinity of LX-96 using bio-layer interferometry (BLI). LX-96 was loaded onto Anti-Mouse IgG Fc Capture (AMC) biosensors and dipped into a solution of varying concentrations of misfolded AL09 (0-200 nM) or native AL09 (0-3000 nM). From the sensorgram, we observed rapid association of misfolded AL09 with LX-96, followed by a slow dissociation step (FIG. 13A). This suggests a very tight binding interaction between the antibody and target. The association and dissociation sensorgrams were fit using the Octet Systems Software, and binding affinity of LX-96 for misfolded AL09 was measured to be 1.119±0.01 nM (FIG. 13A), while no measurable binding was detected for native AL09 at the concentrations assayed (FIG. 13B). We repeated the assay on a different disease-causing kappa light chain variant (AL12) and determined the $K_D$ to be 7.5±0.1 nM for the misfolded form (FIG. 13C), and no meaningful binding for the native form (FIG. 13D). This confirms that LX-96 is capable of binding specifically to the misfolded form of different kappa light chain variants at similar, single-digit nanomolar affinities.

Figures 14A, 14B:
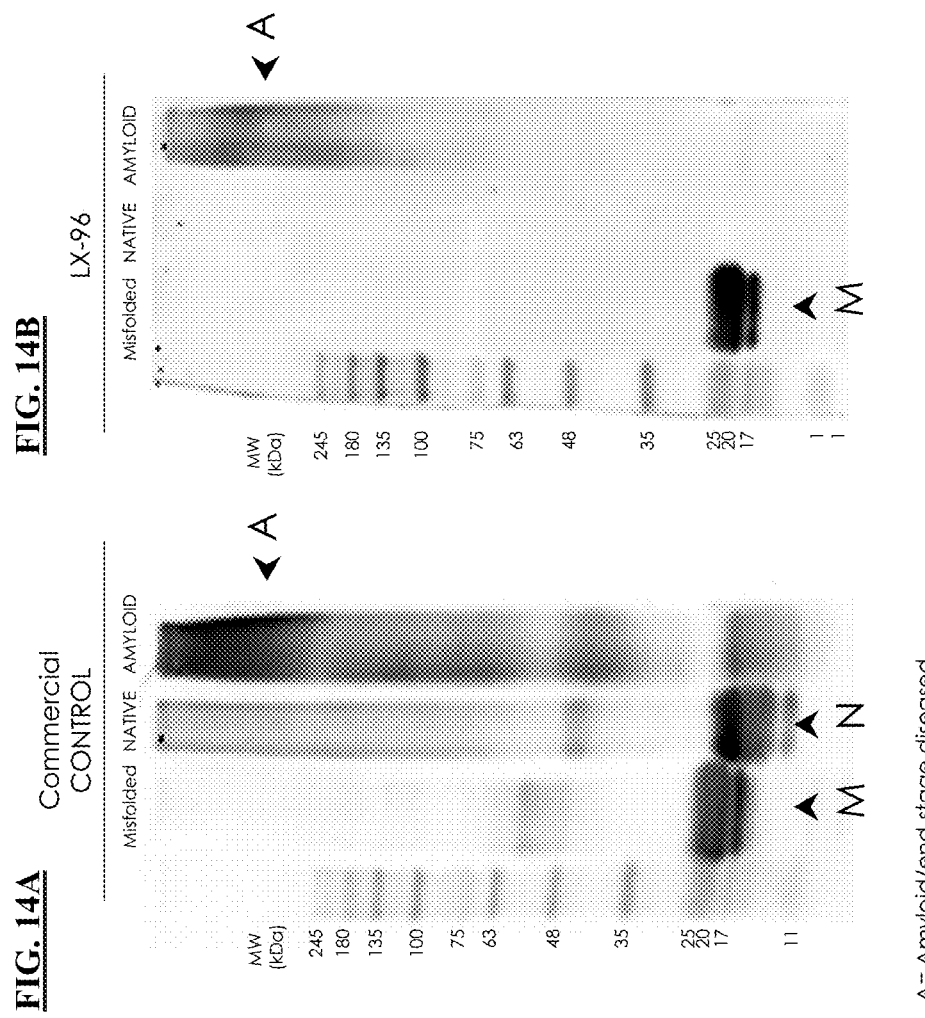
FIGS. 14A-14B are images of native Western blot of misfolded, native, or amyloid species using commercial control antibody (FIG. 14A) or LX-96 (FIG. 14B). Western blots were prepared by transferring from a native SDS-PAGE and detecting using Licor system with appropriate secondary antibodies. Monomeric species of native (N) or misfolded (M) AL09 appear as ~25 kDa bands, while aggregates or large MW species (>250 kDa) appear as a smear in the amyloid (A) and native lanes.

To further validate that LX-96 specifically binds mis/unfolded kappa light chains, native western blots were performed using AL09 in native, mis/unfolded, and amyloid states (FIGS. 14A-14B). The mis/unfolded state of AL09 was generated by unfolding AL09 in 6M guanidine hydrochloride followed by reduction in dithiothreitol and alkylation with iodoacetamide and the amyloid state of AL09 was generated by incubation of AL09 for 5 days, pH 7, 57° C., 500 rpm. Presence of amyloid was confirmed using Thioflavin T (ThT) fluorescence. Western blots were prepared using primary antibody concentrations of 5 µg/mL for LX-96 and DAKO kappa rabbit polyclonal antibody (commercial control). Secondary antibodies (Licor goat anti-mouse 680LT antibody and goat anti-rabbit 680LT) were diluted to 1:10,000 according to manufacturer's instructions. The Western blot analysis indicates that while commercial kappa light chain antibody recognizes all forms (native, mis/unfolded, and amyloid) of AL09, LX-96 recognizes only mis/unfolded, and amyloid forms but not native AL09. Under amyloid-forming conditions, native forms of AL09 are still present in smaller quantities, as detected by the commercial antibody control. These species, however, were also not recognized by LX-96, further demonstrating amyloid-specificity.

Example 7: LX-96 Specifically Recognizes Kappa AL Amyloid Fibrils in Human Tissue We evaluated the reactivity of LX-96 by immunohistochemical analysis of cardiac, hepatic, and pancreatic tissues from validated cases of amyloidosis. In cases of biopsy-confirmed kappa AL amyloidosis, we verified the presence of kappa light chains in the tissues using a non-specific anti-kappa antibody control, and confirmed the on-target staining of LX-96 to kappa AL amyloid deposits in both cases of cardiac kappa AL amyloidosis (FIGS. 15D and 15E) and one case of hepatic kappa AL amyloidosis (FIG. 15B).

We then evaluated cross-reactivity of LX-96 in 3 pathological control tissues. In these cases, distribution of amyloids within the tissue was confirmed by staining using the dye Congo red, or with commercial antibodies (FIGS. 16A-16I). In an ATTR cardiac amyloidosis case, we observed positive Congo red staining of amyloids (FIG. 16A) and non-specific, non-amyloid binding of commercial anti-lambda and anti-kappa light chain antibodies (FIGS. 16B and 16C). LX-96, on the other hand, showed no staining for the cardiac tissue (FIG. 16D). To assess cross-reactivity to lambda AL cardiac amyloid deposits, we first verified the co-staining of the tissue with Congo red and anti-lambda antibodies (FIGS. 16E-16F). Whereas a commercial anti-kappa antibody showed non-specific, non-amyloid binding to this tissue (FIG. 16G), LX-96 showed no cross-reactivity (FIG. 16H). Furthermore, no cross-reactivity was observed in a biopsy-confirmed case of IAPP (islet amyloid polypeptide) amyloidosis (FIG. 16I). Together, this immunohistochemical analysis provides evidence that LX-96 has the capability to specifically bind kappa light chain amyloid deposits ex vivo, with no off-target interactions with native proteins or other non-specific amyloid forms, in a variety of tissues.

Example 8: Cell-Free Inhibition of AL09 Aggregation Via LX-96 Binding

Figure 17:
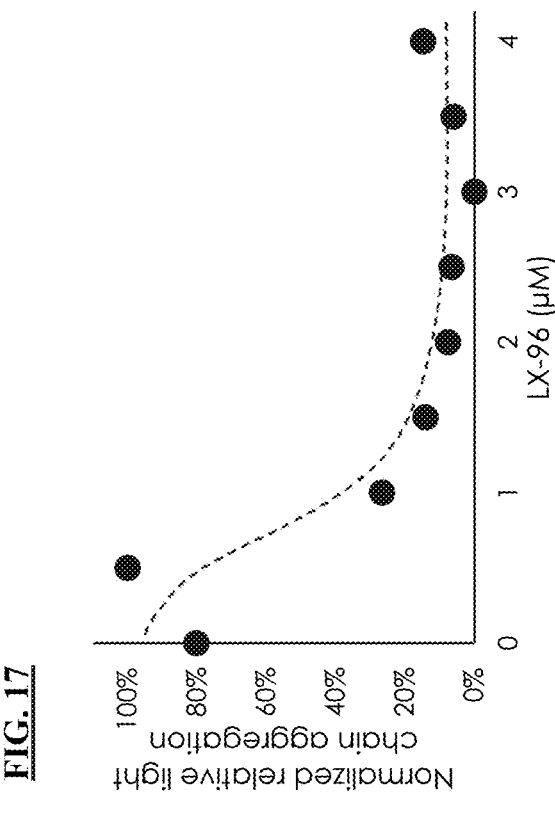
FIG. 17 is a graphical representation of inhibition of AL09 aggregation by LX-96 in vitro. Aggregation of FITC-labeled AL09 in the presence of varying substoichiometric concentrations of LX-96 was measured at endpoint. Aggregation was derived from FITC fluorescence of soluble material by normalization and presented as a percentage, with a trend-line acting as a guide for the eye.

We next evaluated the effects of LX-96 binding in AL09 aggregation in vitro under amyloid-forming conditions. A solution of FITC-labeled AL09 (2% labeled by weight) at a final concentration of 15 μM was treated with low pH (4.0) and agitation at 600 rpm to induce aggregation over 14 h. Aggregation was indirectly measured by the FITC fluorescence of the soluble AL09 fraction following high speed centrifugation to pellet the insoluble, aggregated material. We introduced sub-stoichiometric concentrations (0-4 μM) of LX-96 to AL09 at the beginning of the aggregation process and measured the soluble fraction of AL09 at endpoint. LX-96 was able to inhibit the aggregation of AL09 at sub-stoichiometric concentrations, with an estimated $IC_{50}$ of <1 μM (FIG. 17).

Example 9: LX-96 Induces Antibody-Mediated Phagocytic Uptake of Kappa Light Chain Amyloid in Murine Monocytes Finally, we sought to examine the ability of LX-96 to facilitate immune clearance of AL09 aggregates in vitro. As such, we performed a phagocytosis assay using RAW264.7 (ATCC) murine monocytic cells and AL09 amyloid aggregates labelled with pH-sensitive rhodamine (pHrodo) dye, which increases in fluorescence upon phagocytosis and entry into the lysosome due to the decrease in pH. AL09 amyloid aggregates generated by methods described previously (57° C., 500 rpm, 5 days) were labeled and pre-incubated with either LX-96, an isotype control, or no antibodies and added to RAW264.7 cells for 3 hours at 37° C., 5% $CO_2$, at a final concentrations of 100 μg/mL AL09 and 20 μg/mL of antibodies. Cells were imaged using brightfield and pHrodo fluorescence channels to visualize phagocytic uptake of labeled AL09 amyloid aggregates. By visual assessment, LX-96 significantly increased the number of RAW cells that internalized AL09 aggregates compared to isotype or no antibody controls, as demonstrated by the increase in number of pHrodo-positive cells (FIGS. 18B, 18D and 18F). Quantification of the uptake via mean pHrodo fluorescence per cell confirmed that LX-96 significantly increased phagocytic uptake of AL09 over both the isotype control (p=0.0236) and no antibody control (p=0.0102), indicating a significant increase in clearance of immune complexes (FIG. 18G).

Example 10: LX-96-Dependent Phagocytic Clearance in Murine Amyloidoma Model

Figure 19:
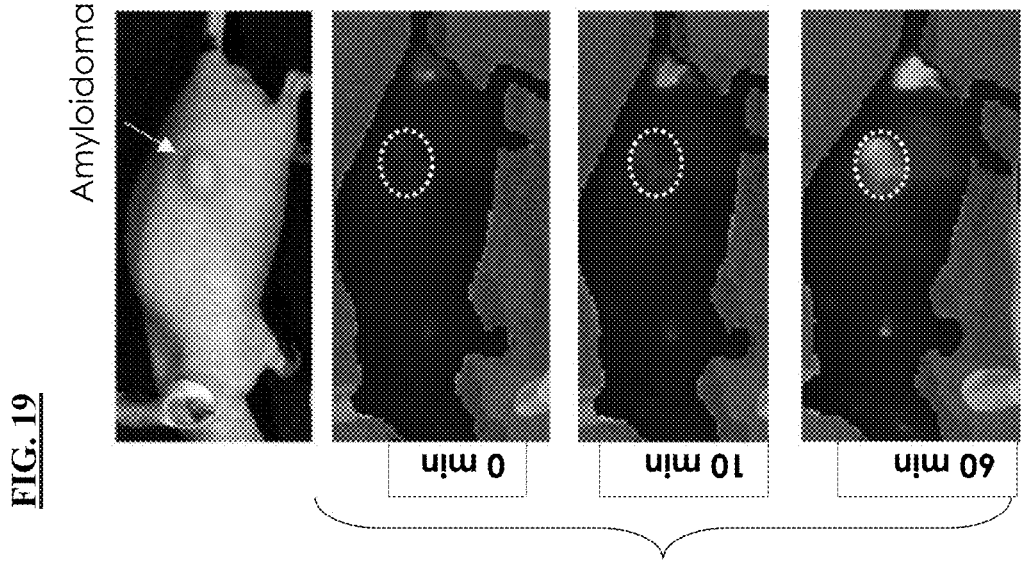
FIG. 19 is a fluorescence image of a mouse implanted with kappa light chain amyloid aggregates (amyloidoma; dotted line) and infused with a single 10 mg/kg dose of fluorescently labeled LX-96 antibody via tail vein injection. The white signal illustrates increased accumulation of LX-96 to the amyloidoma within 60 min of infusion.
Figure 20B:
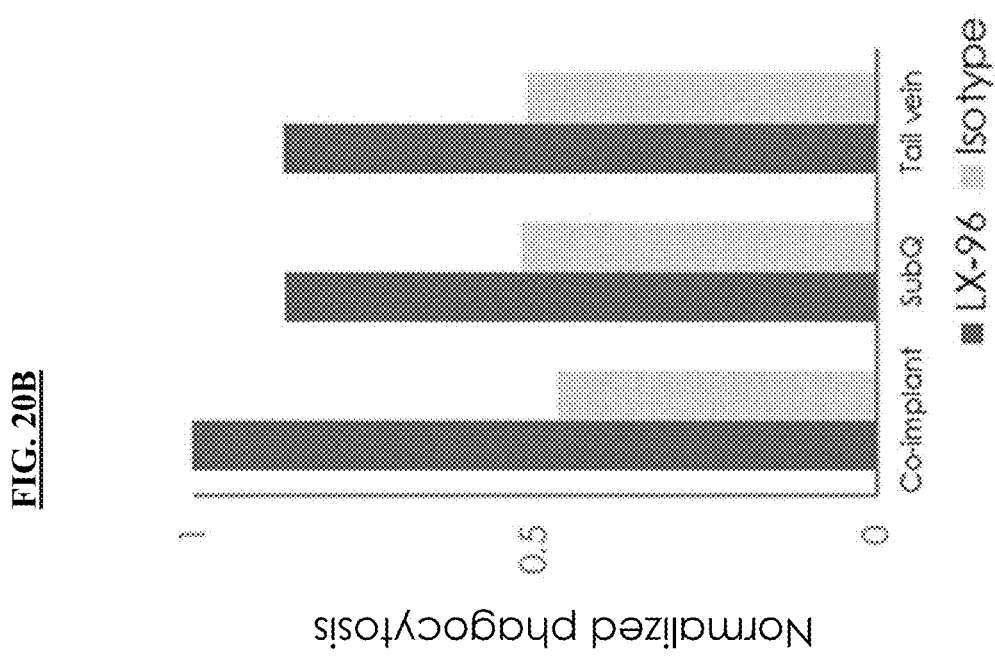
FIG. 20B is the quantified, graphical representations of phagocytosis using three modalities of antibody administration: co-mixing the amyloid with antibodies prior to implantation (co-implant), subcutaneous injection (SubQ) or tail vein injection.
Figure 20A:
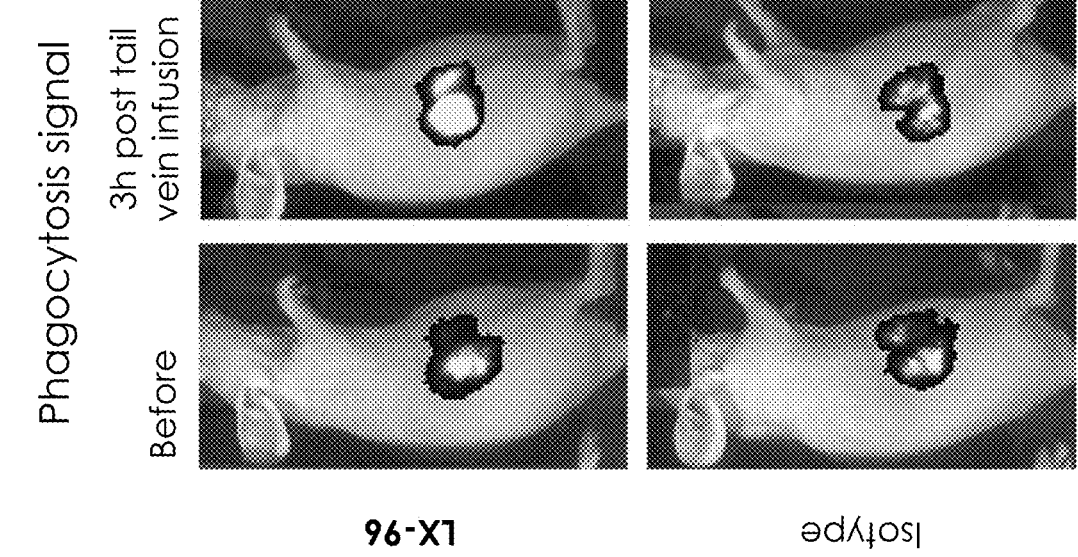
FIG. 20A are fluorescence images of mice implanted with pHrodo-labeled kappa light chain amyloid and 3 hours after a single 10 mg/kg tail vein infusion of LX-96 or isotype antibody control. Increase in signal (white) represents increased phagocytosis.
Figure 22:
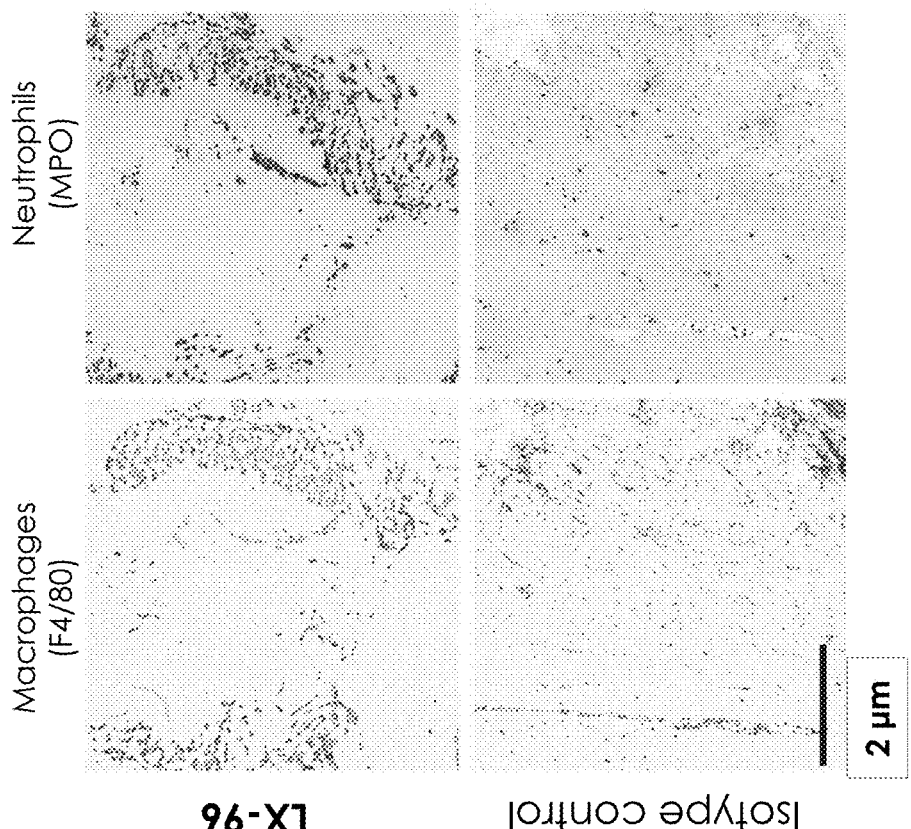
FIG. 22 are immunohistochemistry staining of excised amyloidoma tissue from mice that are either treated with isotype control or LX-96 24 h after infusion. Representative fields of view are shown. Tissues were stained using macrophage marker (F4/80) or neutrophil markers (MPO). Positive staining is shown as black.

We next assessed the ability for LX-96 to induce an immune response in a amyloidoma mouse model using NU/NU mice. We first tracked the distribution of LX-96 using a colocalization assay (FIG. 19). 100 μg of AL09 amyloid was mixed with Matrigel and implanted subcutaneously into the mouse flank to form an amyloidoma. A single dose of fluorescently labeled LX-96 at 10 mg/kg was infused via tail vein injection and the mouse was imaged by over several hours using an IVIS® Spectrum In Vivo Imaging System. We observed co-localization of LX-96 to the amyloidoma within 60 minutes of infusion, suggesting that LX-96 is capable of reaching extracellular amyloid deposits through the bloodstream. We then assessed whether LX-96 can enhance the immune response of the mouse using a phagocytic uptake assay. 100 μg of pHrodo-labeled AL09 amyloid was implanted as previously described, and LX-96 (or isotype antibody control) was administered to the mouse via tail vein injection at a single 10 mg/kg dose. The pHrodo fluorescence was measured after 3 h. Whereas the pHrodo (indicator of phagocytosis) signals were unchanged upon isotype antibody injection, mice with LX-96 injections had a greater increase in phagocytosis signal (FIG. 20A). We repeated the assay using two other antibody delivery modalities: co-mixing with the amyloidoma prior to implantation (co-implant) and direct subcutaneous injection into the amyloidoma (subQ), and observed similar enhancements to phagocytosis, at approximately 2-fold increase in all 3 delivery methods (FIG. 20B). We next measured the rate of amyloid reduction in the presence or absence of LX-96 by implanting two equal sized fluorescently labeled amyloidoma in the same animal (FIG. 21A). In this assay, one amyloidoma was untreated, and the adjacent implant was pre-mixed with LX-96 at 10 mg/kg. The reduction in amyloidoma were measured and quantified over 3 days by fluorescence imaging (FIG. 21B). Although both amyloidoma reduced in size, the rate of reduction was significantly increased (three-fold) by the presence of LX-96, reaching 80% amyloid reduction within 1 day, compared to 3 days in the absence of antibody (FIG. 21C). We further confirmed the mechanism of action of LX-96 by excising the amyloidoma (pre-mixed with either LX-96 or isotype control) and staining the excised tissue by immunohistochemistry using macrophage or neutrophil markers (FIG. 22). The results of the staining suggest that LX-96 enhances phagocytic clearance of the amyloidoma by enhancing the recruitment of macrophages and neutrophils to the site. Together, these in vivo findings suggests that LX-96 is able to enhance phagocytic clearance of deposited amyloid in an animal model.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other aspects of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

All publications, patents, and patent applications disclosed herein are incorporated by reference to the same extent as if each individual publication, patent or patent application was specifically and individually indicated to be incorporated by reference.

What is claimed:

1. An anti-AL09 amyloid antibody, comprising:
   (a) a VL-CDR1 comprising the amino acid sequence set forth in SEQ ID NO: 11;
   (b) a VL-CDR2 comprising the amino acid sequence set forth in SEQ ID NO: 12;
   (c) a VL-CDR3 comprising the amino acid sequence set forth in SEQ ID NO: 13;
   (d) a VH-CDR1 comprising the amino acid sequence set forth in SEQ ID NO: 15;
   (e) a VH-CDR2 comprising the amino acid sequence set forth in SEQ ID NO: 16; and
   (f) a VH-CDR3 comprising the amino acid sequence set forth in SEQ ID NO: 17.

2. The anti-AL09 amyloid antibody of claim 1, comprising a heavy chain variable region comprising an amino acid sequence at least 90% identical to the amino acid sequence set forth in SEQ ID NO: 14.

3. The anti-AL09 amyloid antibody of claim 2, wherein the heavy chain variable region comprises the amino acid sequence set forth in SEQ ID NO: 14.

4. The anti-AL09 amyloid antibody of claim 1, comprising a light chain variable region comprising an amino acid sequence at least 90% identical to the amino acid sequence set forth in SEQ ID NO: 10.

5. The anti-AL09 amyloid antibody of claim 4, wherein the light chain variable region comprises the amino acid sequence set forth in SEQ ID NO: 10.

6. The anti-AL09 amyloid antibody of claim 1, wherein the anti-AL09 amyloid antibody binds to AL09 amyloid with a $K_D$ of between 500 picomolar and 25 nanomolar.

7. A polynucleotide or a plurality of polynucleotides encoding the anti-AL09 amyloid antibody of claim 1.

8. A method for increasing phagocytosis of amyloid deposits in a subject in need thereof comprising administering to the subject an anti-AL09 amyloid antibody comprising:

(a) a VL-CDR1 comprising the amino acid sequence set forth in SEQ ID NO: 11;

(b) a VL-CDR2 comprising the amino acid sequence set forth in SEQ ID NO: 12;

(c) a VL-CDR3 comprising the amino acid sequence set forth in SEQ ID NO: 13;

(d) a VH-CDR1 comprising the amino acid sequence set forth in SEQ ID NO: 15;

(e) a VH-CDR2 comprising the amino acid sequence set forth in SEQ ID NO: 16; and (f) a VH-CDR3 comprising the amino acid sequence set forth in SEQ ID NO: 17, thereby increasing the phagocytosis of the amyloid deposits in the subject.

9. The method of claim 8, wherein the anti-AL09 amyloid antibody comprises a heavy chain variable region comprising an amino acid sequence at least 90% identical to the amino acid sequence set forth in SEQ ID NO: 14.

10. The anti-AL09 amyloid antibody of claim 9, wherein the heavy chain variable region comprises the amino acid sequence set forth in SEQ ID NO: 14.

11. The anti-AL09 amyloid antibody of claim 8, wherein the anti-AL09 amyloid antibody comprises a light chain variable region comprising an amino acid sequence at least 90% identical to the amino acid sequence set forth in SEQ ID NO: 10.

12. The anti-AL09 amyloid antibody of claim 11, wherein the light chain variable region comprises the amino acid sequence set forth in SEQ ID NO: 10.

13. The anti-AL09 amyloid antibody of claim 8, wherein the anti-AL09 amyloid antibody binds to AL09 amyloid with a $K_D$ of between 500 picomolar and 25 nanomolar.

\* \* \* \* \*